(12) United States Patent
Herson

(10) Patent No.: US 10,889,625 B2
(45) Date of Patent: Jan. 12, 2021

(54) PEPTIDE-BASED METHODS FOR TREATING NEUROLOGICAL INJURY

(71) Applicant: THE REGENTS OF THE UNIVERSITY OF COLORADO, a body corporate, Denver, CO (US)

(72) Inventor: Paco S. Herson, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 16/079,519

(22) PCT Filed: Feb. 23, 2017

(86) PCT No.: PCT/US2017/019140
§ 371 (c)(1),
(2) Date: Aug. 23, 2018

(87) PCT Pub. No.: WO2017/147298
PCT Pub. Date: Aug. 31, 2017

(65) Prior Publication Data
US 2019/0048050 A1 Feb. 14, 2019

Related U.S. Application Data

(60) Provisional application No. 62/298,585, filed on Feb. 23, 2016.

(51) Int. Cl.
| | |
|---|---|
| *C07K 14/47* | (2006.01) |
| *G01N 33/566* | (2006.01) |
| *A61K 38/49* | (2006.01) |
| *G01N 33/68* | (2006.01) |
| *A61P 25/28* | (2006.01) |
| *A61K 38/17* | (2006.01) |
| *A61K 45/06* | (2006.01) |
| *C07K 17/08* | (2006.01) |
| *C07K 17/10* | (2006.01) |
| *A61K 31/505* | (2006.01) |
| *A61K 31/37* | (2006.01) |
| *A61K 31/437* | (2006.01) |
| *A61K 31/616* | (2006.01) |
| *A61K 31/727* | (2006.01) |
| *A61K 31/40* | (2006.01) |
| *A61K 47/64* | (2017.01) |
| *A61K 31/401* | (2006.01) |
| *A61K 31/4184* | (2006.01) |
| *A61K 31/4365* | (2006.01) |

(Continued)

(52) U.S. Cl.
CPC .......... *C07K 14/4703* (2013.01); *A61K 31/37* (2013.01); *A61K 31/40* (2013.01); *A61K 31/401* (2013.01); *A61K 31/4184* (2013.01); *A61K 31/437* (2013.01); *A61K 31/4365* (2013.01); *A61K 31/505* (2013.01); *A61K 31/616* (2013.01); *A61K 31/727* (2013.01); *A61K 38/1709* (2013.01); *A61K 38/49* (2013.01); *A61K 45/06* (2013.01); *A61K 47/60* (2017.08); *A61K 47/6455* (2017.08); *A61P 25/28* (2018.01); *C07K 17/08* (2013.01); *C07K 17/10* (2013.01); *C07K 17/14* (2013.01); *G01N 33/566* (2013.01); *G01N 33/6872* (2013.01); *A61K 38/00* (2013.01); *C07K 2319/10* (2013.01); *C07K 2319/30* (2013.01)

(58) Field of Classification Search
CPC ................ C07K 14/4703; C07K 38/04; C07K 2317/70; C07K 2317/76; C07K 2317/77; C07K 17/08; C07K 17/10; C07K 17/14; C07K 2319/10; C07K 2319/30; G01N 33/566; G01N 33/6872; A61P 25/28; A61K 38/16; A61K 38/17; A61K 38/177; A61K 31/505; A61K 38/49; A61K 31/37; A61K 31/437; A61K 31/616; A61K 31/727; A61K 31/40; A61K 47/6455; A61K 31/401; A61K 31/4184; A61K 31/4365; A61K 47/60; A61K 38/1709; A61K 45/06; A61K 38/00; A61K 38/04
See application file for complete search history.

(56) References Cited

U.S. PATENT DOCUMENTS

2004/0235069 A1* 11/2004 Sano .................. G01N 33/5008
435/7.23
2004/0259209 A1 12/2004 Sun et al.
(Continued)

FOREIGN PATENT DOCUMENTS

| JP | WO 2003/033727 | * 4/2003 | ............. G01N 33/50 |
|---|---|---|---|
| WO | 2007082053 A2 | 7/2007 | |

OTHER PUBLICATIONS

The Merck Index entry "Valine", Royal Society of Chemistry, published 2013 (Year: 2013).*

(Continued)

*Primary Examiner* — Kimberly Ballard
*Assistant Examiner* — Stacey N Macfarlane
(74) *Attorney, Agent, or Firm* — Timothy H. Van Dyke; Wolter Van Dyke Davis, PLLC

(57) ABSTRACT

Methods for treating and preventing neurodegenerative disease, neurological injury, including stroke, via administration of Transient receptor potential M2 (TRPM2)-inhibitors. The inhibitors may be administered in conjunction with another therapeutic agent or therapeutic regimen. The peptides may be administered to a human male. The peptides may be administered within eight hours of a neurological injury, such as a stroke.

5 Claims, 12 Drawing Sheets
Specification includes a Sequence Listing.

(51) Int. Cl.
  *A61K 47/60* (2017.01)
  *C07K 17/14* (2006.01)
  *A61K 38/00* (2006.01)

(56) References Cited

U.S. PATENT DOCUMENTS

| | | |
|---|---|---|
| 2008/0119409 A1 | 5/2008 | Fischer et al. |
| 2008/0119412 A1 | 5/2008 | Tymianski et al. |
| 2013/0203715 A1 | 8/2013 | Hava et al. |
| 2014/0228277 A1 | 8/2014 | Lazarus et al. |
| 2014/0274906 A1 | 9/2014 | Tymianski et al. |

OTHER PUBLICATIONS

International Search Report issued by the U.S. Patent and Trademark Office for International Patent Application No. PCT/US2017/019140, dated Aug. 4, 2017, 7 pages.

Written Opinion issued by the U.S. Patent and Trademark Office for International Patent Application No. PCT/US2017/019140, dated Aug. 4, 2017, 10 pages.

PCT/US2017/019140; International Search Report and Written Opinion; dated Aug. 4, 2017; 17 pages.

EP17757210.4; Search Report; dated Jul. 12, 2019; 9 pages.

Jia, J et al., "Sex differences in neuroprotection provided by inhibition of TRPM2 channels following experimental stroke", Journal of Cerebral Blood Flow & Metabolism, 2011, vol. 31, pp. 2160-2168.

Ostapchenko, V.G. et al., "The Transient Receptor Potential Melastatin 2 (TRPM2) Channel Contributes to B-Amyloid Oligomer-Related Neurotoxicity and Memory Impairment", The Journal of Neuroscience, Nov. 2015, vol. 35(45), pp. 15157-15169.

Perraud, Anne-Laure et al., "ADP-ribose gating of the calcium-permeable LTRPC2 channel revealed by Nudix motif homology", Nature, May 2001, vol. 411, pp. 595-599.

Shimixu, T. et al., "Androgen and PARP-1 regulation of TRPM2 channels after ischemic injury", Journal of Cerebral Blood Flow & Metabolism, 2013, vol. 33, pp. 1549-1555.

Shimixu, T. et al., "Extended therapeutic window of a novel peptide inhibitor of TRPM2 channels following focal cerebral ischemia", Exp Neurol, 2016, 16 pages.

Sumoza-Toledo, A. et al., "TRPM2: a multifunctional ion channel for calcium signalling", J Physiol, 2011, vol. 589.7, pp. 1515-1525.

Sun, Yuyang et al., "TRPM2 Promotes Neurotoxin Mpp+/MpTP-Induced Cell Death", Mol. Neurobiol, 2016, 12 pages.

Verma, S. et al., "TRPM2 channel activation following in vitro ischemia contributes to male hippocampal cell death", Neurosci Lett., 2012, vol. 530(1), 12 pages.

Xie, Yu-Feng et al., "TRPM2, calcium and neurodegenerative diseases", Int J Physiol Pathophysiol Pharmacol, 2010, vol. 2(2), pp. 95-103.

* cited by examiner

PEPTIDE-BASED METHODS FOR TREATING NEUROLOGICAL INJURY

RELATED APPLICATION DATA

This application is a national stage application under 35 U.S.C. 371 of PCT Application No. PCT/US2017/019140, having an international filing date of 23 Feb. 2017, which designated the United States, which PCT Application claimed the benefit of U.S. Provisional Patent Application Ser. No. 62/298,585, filed Feb. 23, 2016, both of which are incorporated herein by reference.

SEQUENCE LISTING DATA

The Sequence Listing text file attached hereto, created Feb. 23, 2016, size 3 kilobytes, filename "2848-202_Sequence_listing_ST25" is incorporated herein by reference in its entirety.

BACKGROUND

Stroke is the second leading cause of death worldwide with a significant financial burden and poor life quality among recovered patients due to cognitive disability. Unfortunately, the pharmacological tools available to reduce brain injury and treat patients with stroke are extremely limited. Two of the most important and non-modifiable risk factors for stroke are age and gender, with the risk for stroke doubling every decade after age 55 years, and affecting men to a larger extent than women until later in life where the rate of stroke increases in elderly women. This latter observation is likely due to effects of androgens and estrogen in cell death pathways. However, most neuroprotection investigations (pre-clinical or clinical) either have not used female animals or have not been powered to find differences between sexes in human trials. Thus, it is critical to more accurately model the human patient population in order to determine the therapeutic potential of any new compounds.

Transient receptor potential M2 (TRPM2) is a member of the superfamily of transient receptor potential (TRP) channels. These channels are believed to have six transmembrane domains and intracellular amino- and carboxy-termini. TRP channels are grouped into three families based up on sequence homology and particular structural motifs (Harteneck et al., 2000, Trends Neurosci., 23:159; Montell et al., 2002, Mol. Cell., 9:229). TRPM2 belongs to family M, named after the founding member, melastatin. TRPM channels are characterized by complex structural sub-regions in their amino- and carboxy-termini, which carry additional functionality such as kinase activity (Ryazanov, 2002, FEBS Lett., 514:26). There is limited information regarding the expression and function of TRPM2. High levels of expression were detected in the nervous system and lower levels in peripheral tissues such as bone marrow, spleen, lung and heart (Nagamine et al., 1998, Genomics, 54:124; Perraud et al., 2001, Nature, 411:595). TRPM2 channels are non-selective cation channels activated by ADP ribose (ADPr). ADPr may be generated by PARP-1 in response to oxidative stress and cerebral ischemia, which is particularly relevant in the setting of reperfusion injury after ischemia. Inhibition of TRPM2 ion channels with clotrimazole (CTZ) or genetic knockdown reduces infarct size in males, but not females, following stroke. While TRPM2 appears to be a viable target for therapeutic interventions for stroke in males, preclinical studies have been limited by the lack of a specific inhibitor.

SUMMARY

Because the modulation of TRPM2 ion channels has been shown to be significantly associated with cause and/or control of certain disorders and diseases, it is necessary to find agents which are safe and efficacious in inhibiting TRPM2 ion channels.

TRPM2 channels have been implicated in ischemic neuronal damage for over a decade (for review, see Aarts M M, Tymianski M. *Trpms and neuronal cell death.* Pflugers Arch—Eur J Physiol. 2005; 451:243-249; see also US Patent Publication No. 2010/0298394, Nov. 25, 2010), yet the field has been plagued by lack of an inhibitor specific for the channel. Non-specific TRPM2 inhibitors, such as clotrimazole (CTZ), have been shown to reduce neuronal death in in vitro cortical and hippocampal neurons to reduce injury in male animals following focal and global cerebral ischemia. The present inventors have identified novel and specific peptide inhibitors of TRPM2 channels.

A distinguishing property of TRPM2 channels is that they are gated by ADPribose (ADPr), via binding to an ADPr hydrolase homology domain (termed "NUDT9-H") in the C-terminus. The catalytic domain of NUDT9-H is the Nudix domain, which, in coordination with several distant amino acids within the same domain, form the ADPr binding pocket. The inventors targeted the ADPr binding pocket as a strategy to inhibit TRPM2 channel activation. Expression of channels lacking the C-terminal Nudix homology domain are inactive. Therefore, the inventors generated peptides, including GSREPGEMLPRKLKRVLRQEFWV (SEQ ID NO:1; "M2NX"), fused to the cell permeable TAT sequence, YGRKKRRQRRR (SEQ ID NO:2; "tat 47-57") to form the 34-mer, YGRKKRRQRRRGSREPGEML-PRKLKRVLRQEFWV (SEQ ID NO:3; "tat-M2NX"), which specifically inhibits TRPM2 channel activity via interaction with the ADPr binding pocket of the NUDT9-H domain of the channel.

Importantly, primary data disclosed herein shows that inhibition of TRPM2 channels improves functional recovery following stroke, traumatic brain injury, cardiac arrest-induced global ischemia and neurodegenerative disease. These effects are observed in both male and female animals and when TRPM2 inhibition is accomplished during the acute or chronic timepoints.

Thus, this disclosure provides methods of treating or preventing neurological damage or injury, or neurodegenerative diseases, or enhancing the restoration of neurological function, in a subject, by administering a pharmaceutical composition comprising a TRPM2-inhibitory peptide of this disclosure, to the subject.

This disclosure also provides methods of treating or preventing neurological damage or injury, or neurodegenerative diseases, or enhancing the restoration of neurological function, in a subject, by administering a pharmaceutical composition comprising a TRPM2-inhibitory peptide of this disclosure, or variants thereof, and at least one additional therapeutic agent to the subject. The additional therapeutic agent(s) may be one or more neuroprotective, neurorestorative or blood clot preventing or dissolving agents.

In these methods, the administration may be by parenteral administration. In these methods, the peptide may be administered at a dosage of about 0.05 to about 25 mg/kg. In these methods, the subject may be a human. The subject may be a male.

One aspect is a pharmaceutical composition comprising a peptide of this disclosure, or a multimer, derivative, or variant thereof, and a pharmaceutically acceptable carrier for the treatment or prevention of neurological damage or injury, or neurodegenerative diseases, or enhancing the restoration of neurological function. These compositions may include at least one additional therapeutic agent, and therefore another aspect is a pharmaceutical composition comprising a peptide of this disclosure, or a multimer, derivative, or variant thereof, at least one additional therapeutic agent, and a pharmaceutically acceptable carrier for the treatment or prevention of neurological damage or injury, including stroke. A related aspect is the use of a peptide of this disclosure or a multimer, derivative, or variant thereof, for the treatment or prevention of neurological damage or injury, including stroke.

Other aspects of this disclosure are described in or are obvious from the following disclosure and are within the ambit of this disclosure.

BRIEF DESCRIPTION OF THE FIGURES

The following Detailed Description, given by way of Examples, but not intended to limit this disclosure to specific embodiments described, may be understood in conjunction with the accompanying figures, in which:

FIG. 6A is a diary plot of male responses to TBS. Arrow indicates timing of TBS (40 pulses). FIG. 6B shows quantification of change from baseline in male (blue) and female (red). *P<0.05 compared to sham control.

FIG. 7A shows quantification of ischemic neurons in CA1 region of hippocampus 3 days after CA/CPR, *P<0.05. FIG. 7B shows that tat-M2NX prevents ischemia-induced impairment of synaptic plasticity. Arrow indicates timing of TBS (40 pulses).

FIG. 8A is a diary plot of male responses to TBS. Arrow indicates timing of TBS (40 pulses). FIG. 8B shows the quantification of change from baseline in male (blue) and female (red).

FIG. 9A is a diary plot of male responses to TBS. Arrow indicates timing of TBS (40 pulses). FIG. 9B shows quantification of change from baseline in male (blue) and female (red). *P<0.05 compared to sham control.

FIG. 10A shows the quantification of freezing behavior on day 8, 24 hrs after exposure to novel context and foot shock. CA/CPR mice injected with tat-SCR scrambled peptide exhibit reduced freezing behavior, consistent with impaired memory of the context. In contrast, tat-M2NX treated mice (on day 7) have increased freezing. FIG. 10B shows impaired contextual fear conditioning behavior 30 days after CA/CPR.

FIG. 8A is a diary plot of responses to exposure to amyloid-beta. FIG. 12B shows synaptic plasticity quantification as percent of change from baseline.

DETAILED DESCRIPTION

Figure 1A:
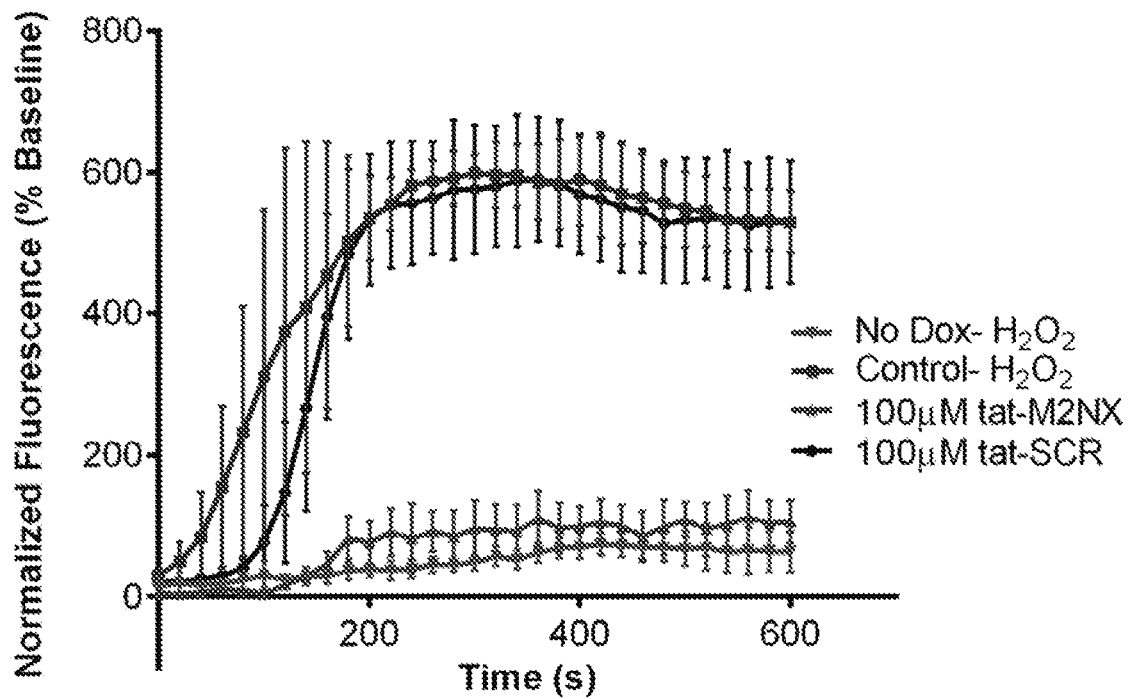
FIG. 1A shows tat-M2NX inhibits Ca2+ influx through TRPM2 channels and provides in vivo neuroprotection, as average fluorescent changes in Fluo-5F fluorescence, shown as percentage increase from baseline, in HEK-293 cells expressing tetracycline-regulated cytomegalovirus-driven transcription of FLAG-tagged human TRPM2. Samples were treated with 100 μM tat-M2NX (triangles) or tat-SCR (circles) in the presence of 200 μM $H_2O_2$.

As discussed above, this disclosure relates to TRPM2 inhibitors that act to disrupt the ligand (ADPribose)-binding pocket of the TRPM2 channel, thereby preventing activation. Therefore, this disclosure contemplates small molecules that disrupt the ADPr binging portion of the TRPM2 channel.

In one aspect, this disclosure relates to peptides and peptide constructs that are neuroprotective and neurorestorative, and the use of these peptides, and methods of administering such peptides to a subject suffering a neurological injury, neurological disorder, or neurodegenerative disease, or at risk of sustaining a neurological injury, or developing a neurological disorder or neurodegenerative disease.

Definitions

As used herein, the singular forms "a", "and", and "the" include plural referents, unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this technology belongs unless clearly indicated otherwise.

The terms "peptide" and "polypeptide" are used synonymously herein to refer to polymers constructed from amino acid residues.

"Substantially pure", as used herein (for example, in the context of a pharmaceutical composition), means that the peptide makes up greater than about 50% of the total content of the composition (e.g., total protein of the composition), or greater than about 80% of the total protein content. For example, a "substantially pure" peptide refers to compositions in which at least 80%, at least 85%, at least 90% or more of the total composition is the peptide (e.g. 95%, 98%, 99%, greater than 99% of the total protein). The peptide may make up greater than about 90%, greater than about 95%, greater than 98%, or greater than 99%, of the total protein in the composition. In some embodiments, a peptide is substantially pure when the peptide is at least 60% or at least 75% by weight free from organic molecules with which it is associated during production. In some embodiments, the peptide is at least 60%, at least 75%, at least 80%, at least 85%, at least 90%, at least 95%, or at least 99%, by weight, pure. For example, in some embodiments, an immunomodulatory peptide is substantially pure when the immunomodulatory peptide is at least 60% or at least 75% by weight free from organic molecules with which the peptide(s) is associated during production, in some embodiments, the immunomodulatory peptide is at least 60%, at least 75%, at least 80%, at least 85%, at least 90%, at least 95%, or at least 99%, by weight, pure.

The terms "subject", "patient", and "individual", are used herein interchangeably, and refer to a multicellular animal (including mammals (e.g., humans, non-Human primates, murines, ovines, bovines, ruminants, lagomorphs, porcines, caprines, equines, canines, felines, ayes, etc.), avians (e.g., chicken), amphibians (e.g. *Xenopus*), reptiles, and insects (e.g. *Drosophila*). "Animal" includes guinea pig, hamster, ferret, chinchilla, mouse, and rat. These terms specifically include humans, and specifically include male mammals, and therefore, human males.

The term "neuroprotective" as used herein, refers to any property of a peptide that may be evaluated, and/or, that reduces or inhibits, or would be expected to reduce or inhibit, death, apoptosis, destruction or injury to a neuron and/or reduces or inhibits neurodegeneration in a subject.

The term "neurorestorative" as used herein, refers to any property of a peptide that may improve brain function, synaptic function, neuron firing, brain network function, independent of changes in cell death. Neurorestorative applies to agents administered near the time of injury or at chronic timepoints to reverse stable deficits in brain function.

An "effective amount" refers to an amount effective, at dosages and for periods of time necessary, to achieve the desired therapeutic or prophylactic result. A "therapeutically effective amount" of a peptide or pharmaceutical composition comprising a peptide of this disclosure may vary according to factors such as the disease state, age, sex, and weight of the individual, and the ability of the peptide or composition to elicit a desired response in the individual. A therapeutically effective amount is also one in which any toxic or detrimental effects of the peptide or composition comprising the peptide are outweighed by the therapeutically beneficial effects.

Reference herein to any numerical range (for example, a dosage range) expressly includes each numerical value (including fractional numbers and whole numbers) encompassed by that range. For example, but without limitation, reference herein to a range of 0.5 mg/kg to 100 mg/kg explicitly includes all whole numbers of and fractional numbers between the two.

An individual referred to as "suffering from" neurological injury, including stroke, TBI, cardiac arrest, as described herein, has been diagnosed with and/or displays one or more symptoms of neurological injury, including stroke.

As used herein, the term "at risk" for a neurological injury, including stroke, refers to a subject (e.g., a human) that is predisposed to developing stroke and/or expressing one or more symptoms of the disease. This predisposition may be genetic or due to other factors. It is not intended that the present disclosure be limited to any particular signs or symptoms. Thus, it is intended that the present disclosure encompasses subjects that are experiencing any range of neurological injury, including stroke, from sub-clinical to full-blown, wherein the subject exhibits at least one of the indicia (e.g., signs and symptoms) associated with neurological injury, including stroke.

The terms "treat," "treatment," or "treating", as used herein, refer to any method used to partially or completely alleviate, ameliorate, relieve, inhibit, prevent, delay onset of, reduce severity of and/or reduce incidence of one or more symptoms or features of a disease, disorder, and/or condition (e.g., neurological injury, neurodegenerative disease). Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The terms "comprises" and "comprising", have the broad meaning ascribed to them in Patent Law and may mean "includes", "including" and the like.

This disclosure may be understood more fully by reference to the following detailed description and illustrative examples, which are intended to exemplify non-limiting embodiments of this disclosure.

Polypeptides

Peptides of this disclosure include fragments of the Nudix domain of the NUDT9-H region of the C-terminus of TRPM2 channels, or variants thereof, which specifically inhibit the TRPM2 channel activity via interaction with the ADPr binding pocket of the NUDT9-H domain of the channel. Thus, a subject peptide of this disclosure is GSREPGEMLPRKLKRVLRQEFWV (SEQ ID NO:1). Any of the peptides of this disclosure may be linked, preferably at the N-terminus, to an internalization peptide that facilitates translocation through the plasma membrane of a cell. Examples of these peptides include TAT derived from HIV (Vives et al., 1997, J. Biol. Chem. 272:16010; Nagahara et al., 1998, Nat. Med. 4:1449), antennapedia from *Drosophila* (Derossi et al., 1994, J. Biol. Chem. 261:10444), VP22 from herpes simplex virus (Elliot and D'Hare, 1997, Cell 88:223-233), complementarity-determining regions (CDR) 2 and 3 of anti-DNA antibodies (Avrameas et al., 1998, Proc. Natl. Acad. Sci. U.S.A., 95:5601-5606), 70 KDa heat shock protein (Fujihara, 1999, EMBO J. 18:411-419) and transportan (Pooga et al., 1998, FASEB J. 12:67-77). For example, the HIV TAT internalization peptide YGRKKRRQRRR (SEQ ID NO:2) may be used. One exemplary peptide of this disclosure, which includes the HIV Tat internalization peptide and an active peptide inhibitor of TRPM2 channel activity is:
YGRKKRRQRRR-GSREPGEMLPRKLKRVLRQEFWV (SEQ ID NO:3, "Tat-M2NX").

Variants of the standard TAT sequence YGRKKRRQRRR (SEQ ID NO:2) may also be used. Although practice of this disclosure is not dependent on an understanding of mechanism, it is believed that both the capacity to cross membranes and binding to N-type calcium channels of TAT are conferred by the unusually high occurrence of positively charged residues Y, R and K in the peptide. Variant peptides for use in this disclosure should retain ability to facilitate uptake into cells but have reduced capacity to bind N-type calcium channels. Some suitable internalization peptides comprise or consist of an amino acid sequence XGRKKRRQRRR (SEQ ID NO:4), in which X is an amino acid other than Y. A preferred TAT variant has the N-terminal Y residue substituted with F. Thus, a TAT variant comprising or consisting of FGRKKRRQRRR (SEQ ID NO:5) may be used. Another preferred variant of the TAT internalization peptide consists of GRKKRRQRRR (SEQ ID NO:6). If additional residues flanking XGRKKRRQRRR (SEQ ID NO:4) are present (beside the active peptide), the residues may be for example, natural amino acids flanking this segment from a TAT protein, spacer or linker amino acids of a kind typically used to join two peptide domains, e.g., Gly(Ser)$_4$ (SEQ ID NO:7), TGEKP (SEQ ID NO:8), GGRRGGGS (SEQ ID NO:9), or LRQRDGERP (SEQ ID NO:10) (see, e.g., Tang et al. (1996), J. Biol. Chem. 271, 15682-15686; Hennecke et al. (1998), Protein Eng. 11, 405-410)), GSRVQIRCRFRNSTR (SEQ ID NO:11) (see U.S. Patent Publication No. 2014/0235553; Aug. 21, 2014), or may be any other amino acids that do not detectably reduce capacity to confer uptake of the variant without the flanking residues and do not significantly increase inhibition of N-type calcium channels relative to the variant without the flanking residues. Preferably, the number of flanking amino acids, other than an active peptide, does not exceed ten residues on either side of XGRKKRRQRRR (SEQ ID NO:4). Preferably, no flanking amino acids are present and the internalization peptide is linked at its C-terminus directly to an active TRPM2 inhibitor peptide of this disclosure.

A "variant" of a peptide described herein is a polypeptide that is substantially similar to a polypeptide disclosed herein and retains at least one TRPM2 inhibitor property or neuroprotective activity of the peptides of this disclosure. Variants may include deletions (i.e., truncations) of one or more amino acid residues at the N-terminus or the C-terminus of a polypeptide disclosed herein; deletion and/or addition of one or more amino acid residues at one or more internal sites in the polypeptide disclosed herein; and/or substitution of one or more amino acid residues at one or more positions in the polypeptide disclosed herein. For polypeptides that are 12 amino acid residues in length or shorter, variant polypeptides preferably include three or fewer (e.g., two, one, or none) deleted amino acid residues, whether located internally, at the N-terminal end, and/or at the C-terminal end.

Accordingly, the inventive methods and compositions are likewise contemplated for neuroprotective polypeptides that are at least 50% identical (e.g., have at least 60%, 70%, 80%, 90%, 95% or more sequence identity) to the TRPM2 inhibitory polypeptides disclosed herein and that retain at least one neuroprotective property of SEQ ID NO:3. Ordinarily, a protein variant of the neuroprotective peptides of this disclosure will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence protein sequence as disclosed herein, or any other specifically defined fragment of a full-length protein sequence as disclosed herein. Optionally, the variant polypeptides will have no more than one conservative amino acid substitution as compared to the native protein sequence, alternatively no more than 2, 3, 4, 5, 6, 7, 8, 9, or 10 conservative amino acid substitutions as compared to the native protein sequence.

Substituted amino acid residues may be unrelated to the amino acid residue being replaced (e.g., unrelated in terms or hydrophobicity/hydrophilicity, size, charge, polarity, etc.), or the substituted amino acid residues may constitute similar, conservative, or highly conservative amino acid substitutions. As used herein, "similar," "conservative," and "highly conservative" amino acid substitutions are defined as shown in the table, below. The determination of whether an amino acid residue substitution is similar, conservative, or highly conservative is based exclusively on the side chain of the amino acid residue and not the peptide backbone, which may be modified to increase peptide stability, as discussed below.

| Amino Acid Subject Polypeptide | Similar Amino Acid Substitutions | Conservative Amino Acid Substitutions | Highly Conservative Amino Acid Substitutions |
| --- | --- | --- | --- |
| Glycine (G) | A, S, N | A | n/a |
| Alanine (A) | S, G, T, V, C, P, Q | S, G, T | S |
| Serine (S) | T, A, N, G, Q | T, A, N | T, A |
| Threonine (T) | S, A, V, N, M | S, A, V, N | S |
| Cysteine (C) | A, S, T, V, I | A | n/a |
| Proline (P) | A, S, T | A | n/a |
| Methionine (M) | L, I, V, F | L, I, V | L, I |
| Valine (V) | I, L, M , T, A | I, L, M | I |
| Leucine (L) | M, I, V, F, T, A | M, I, V, F | M, I |
| Isoleucine (I) | V, L, M, F, T, C | V, L, M, F | V, L, M |
| Phenylalanine (F) | W, L, M, I, V | W, L | n/a |
| Tyrosine (Y) | F, W, H, L, I | F, W | F |
| Tryptophan (W) | F, L, V | F | n/a |
| Asparagine (N) | Q | Q | Q |
| Glutamine (Q) | N | N | N |
| Aspartic Acid (D) | E | E | E |
| Glutamic Acid (E) | D | D | D |
| Histidine (H) | R, K | R, K | R, K |
| Lysine (K) | R, H | R, H | R, H |
| Arginine (R) | K, H | K, H | K, H |

Conservative amino acid substitutions in the context of a subject peptide are selected so as to preserve activity of the peptide.

Modified Polypeptides

Also contemplated in the context of the inventive methods and compositions is the modification of any neuroprotective polypeptides described herein, by chemical or genetic means. Examples of such modification include construction of peptides of partial or complete sequence with non-natural amino acids and/or natural amino acids in L or D enantiomeric forms. For example, any of the peptides disclosed herein, and any variants thereof, could be produced in an all-D form. Furthermore, the polypeptides may be modified to contain carbohydrate or lipid moieties, such as sugars or fatty acids, covalently linked to the side chains or the N- or C-termini of the amino acids. In addition, the polypeptides may be modified by glycosylation and/or phosphorylation.

In addition, the polypeptides may be modified to enhance solubility and/or half-life upon being administered. For example, polyethylene glycol (PEG) and related polymers have been used to enhance solubility and the half-life of protein therapeutics in the blood. Accordingly, the polypeptides of this disclosure may be modified by PEG polymers and the like. PEG or PEG polymers means a residue containing poly(ethylene glycol) as an essential part. Such a PEG can contain further chemical groups which are necessary for the therapeutic activity of the peptides of this disclosure; which results from the chemical synthesis of the molecule; or which is a spacer for optimal distance of the parts of the molecule from one another. In addition, such a PEG can consist of one or more PEG side-chains which are linked together. PEG groups with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEGs usually have 2 to 8 arms and are described in, for example, U.S. Pat. No. 5,932,462. Especially preferred are PEGs with two PEG side-chains (PEG2) linked via the primary amino groups of a lysine (Monfardini, C, et al., Bioconjugate Chem. 6 (1995) 62-69). The term "PEG" is used broadly to encompass any polyethylene glycol molecule, wherein the number of ethylene glycol (EG) units is at least 460, preferably 460 to 2300 and especially preferably 460 to 1840 (230 EG units refers to a molecular weight of about 10 kDa). The upper number of EG units is only limited by solubility of the PEGylated peptides of this disclosure. Usually PEGs which are larger than PEGs containing 2300 units are not used. Preferably, a PEG used in the invention terminates on one end with hydroxy or methoxy (methoxy PEG, mPEG) and is on the other end covalently attached to a linker moiety via an ether oxygen bond. The polymer is either linear or branched. Branched PEGs are e.g. described in Veronese, F. M., et al., Journal of Bioactive and Compatible Polymers 12 (1997) 196-207. Suitable processes and preferred reagents for the production of PEGylated peptides and variants of this disclosure are described in US Patent Pub. No. 2006/0154865. It is understood that modifications, for example, based on the methods described by Veronese, F. M., Biomaterials 22 (2001) 405-417, can be made in the procedures so long as the process results in PEGylated peptides of this disclosure. Particularly preferred processes for the preparation of PEGylated peptides of this disclosure are described in US 2008/0119409, which is incorporated herein by reference.

Additionally or alternatively, the peptides of this disclosure may be is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, Nature 337:525-31). When constructed together with a therapeutic protein of this disclosure, an Fc domain can provide longer half-life or incorporate such functions as Fc receptor binding, protein A binding, complement fixation, and perhaps even blood-brain barrier, or placental transfer. In one example, a human IgG hinge, CH2, and CH3 region may be fused at either the amino-terminus or carboxyl-terminus of the peptides of this disclosure using methods known to the skilled artisan. The resulting fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

The polypeptides may also be modified to contain sulfur, phosphorous, halogens, metals, etc. Amino acid mimics may be used to produce polypeptides, and therefore, the polypeptides of this disclosure may include amino acid mimics that have enhanced properties, such as resistance to degradation. For example, the polypeptides may include one or more (e.g., all) peptide monomers.

This disclosure also provides nucleic acid molecules which encode a neuroprotective peptide of this disclosure, preferably an active inhibitor of the TRPM2 ion channel, as defined herein and which has at least about 80% nucleic acid sequence identity with a nucleic acid sequence encoding a full-length inhibitor peptide sequence of this disclosure. Ordinarily, a variant polynucleotide of this disclosure will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length TRPM2 inhibitor protein sequence as disclosed herein. Variants do not encompass the native nucleotide sequence.

Ordinarily, variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, or 130 nucleotides in length, wherein in this context the term "about" means the referenced nucleotide sequence length plus or minus 10% of that referenced length. Variant polypeptides of this disclosure may be those that are encoded by a variant polynucleotide of this disclosure.

These polynucleotides may include control sequences, which are DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

This disclosure also provides isolated peptide inhibitors of the TRPM2 ion channel. "Isolated," when used to describe the various peptides disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the protein natural environment will not be present. Ordinarily, however, isolated polypeptide will be prepared by at least one purification step.

The peptides of this disclosure may include "epitope tagged" peptides, which refers to a chimeric polypeptide comprising a TRPM2 inhibitor peptide of this disclosure fused to a "tag polypeptide." The tag polypeptide has enough residues to provide an epitope against which an antibody can be made, yet is short enough such that it does not interfere with activity of the inhibitory polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The peptides of this disclosure may be linked to or associated with a "solid phase" or "solid support" which is a non-aqueous matrix to which a peptide of this disclosure can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

"Active" or "activity" for the purposes herein refers to peptides that inhibit the activity of a TRPM2 ion channel, such as reducing the flux of calcium ions across the TRPM2 ion channel. This disclosure also provides "antagonists" of TRPM2 ion channels, including any molecule that partially or fully blocks, inhibits, or neutralizes a biological activity of a native TRPM2 protein disclosed herein. Suitable antagonist molecules specifically include antagonist antibodies or antibody fragments, fragments or amino acid sequence variants of native TRPM2 proteins, peptides, antisense oligonucleotides, small organic molecules, etc. Methods for identifying antagonists of a TRPM2 protein may comprise contacting a TRPM2 protein with a candidate antagonist molecule and measuring a detectable change in one or more biological activities normally associated with the TRPM2 ion channel protein.

Treatment/Therapy

In certain embodiments, the present disclosure provides methods and compositions to treat (e.g., alleviate, ameliorate, relieve, stabilize, delay onset of, inhibit progression of, reduce severity of, and/or reduce incidence of) and/or prevent stroke, TBI or cardiac arrest or one or more symptoms associated with stroke, brain injury or neurological damage following stroke, brain injury in a subject. The methods and compositions are also useful to treat and/or prevent neurological damage resulting from cerebral ischemia, for example global cerebral ischemia following cardiac arrest. The methods and compositions are also useful to treat traumatic brain injury (TBI). Additionally, the methods and compositions may also be useful to aide in a patient's recovery from these neurological injuries, for example by improving synaptic function and memory in a patient recovering or rehabilitating following a neurological injury or during an active or prescribed rehabilitation program. Indeed, data indicates that delayed administration of the active peptides of this disclosure improves memory in both males and females following stroke, cardiac arrest, and TBI.

Additionally or alternatively, the methods and compositions may be useful to treat and/or prevent a neurodegenerative disorder, peripheral neuropathy, or neuropathic pain, wherein the neurodegenerative disorder is selected from Alzheimer's Disease, Multiple Sclerosis, HIV-associated dementia, Huntington's Disease, Parkinson's Disease, and Amyotrophic Lateral Sclerosis. Data indicates that TRPM2 channels play a role in the development of neurodegenerative diseases, as TRPM2 channels are activated under conditions of oxidative stress and consequently contribute to injury and dysfunction. For example, Parkinson's Disease and Alzheimer's Disease are both neurodegenerative disorders in which oxidative stress has been strongly implicated, making a role for TRPM2 in the etiology of these disorders logical. Thus, this disclosure also provides methods and compositions that are useful in treating and/or preventing neurodegenerative disorders including Parkinson's Disease and Alzheimer's Disease.

Additionally or alternatively, the methods and compositions may be useful to enhance cognitive function in a subject. For example, the methods and compositions may be administered to a subject to enhance synaptic function and/or enhance memory. These effects may reduce or slow the progress of a neurodegenerative disorder, or enhance recovery from a neurological injury.

Additionally or alternatively, the methods and compositions may be useful to treat and/or prevent inflammation, ischemia, atherosclerosis, asthma, autoimmune disease, diabetes, arthritis, allergies, transplant rejection, infection, pain from diabetic neuropathy, gastric pain, postherpetic neuralgia, fibromyalgia, surgery, or chronic back pain.

In these methods, the subject may be human. The subject may be male or female. In specific embodiments, the subject may be a human male.

These treatment methods comprise administering to a subject a pharmaceutical composition comprising a peptide of this disclosure. In certain embodiments, the treatment methods further comprise inhibiting the activity of TRPM2 in the subject (by at least 10% (e.g., 15%, 20%, 25%, 30%, 35%, 40%, 45%, 50%, or more).

These methods may include the administration of a peptide of this disclosure to a subject having a neurological injury, including a stroke, or suspected of having a neurological injury, after the injury has been sustained by the subject. The peptide may be first administered to the subject within a month of the time the neurological injury occurred. Preferably, the peptide is first administered to the subject within 96 hours, or 8 days, of the time the neurological injury occurred. More preferably, the peptide is first administered within a time period of 1 hour to 96 hours of the time neurological injury occurred. More preferably, the peptide is first administered within a time period of 1 minute to 5 hours of the time the neurological injury occurred.

Combination Therapy

Additionally, disclosed herein are methods of treatment (and compositions) in which the neuroprotective peptides of this disclosure (or pharmaceutical compositions comprising such peptides) may be administered in combination with at least one other drug or therapy currently known or later discovered to be effective in the prevention and/or treatment of stroke, or neurological damage following stroke. The drug may be an anticoagulant or clot-dissolving medicine, such as aspirin, clopidogrel or tissue plasminogen activator (tPA). The drug may be an ACE Inhibitor, such as Lisinopril, or a blood thinner, such as warfarin, or heparin, or apixaban, or a statin, such as atorvastatin or rosuvastatin, or irbesartan, or reteplase, or alteplase.

Contemplated therapies include surgery, such as carotid endarterectomy, or angioplasty, or stent placement. Contemplated therapies may also include physical or mental rehabilitation programs, which have proven particularly efficacious for rehabilitation and recovery following stroke and traumatic brain injury.

The neuroprotective/neurorestorative peptides of this disclosure may be administered prior to, concurrently with, or after the administration of the additional drug and/or therapy. These methods may include a step of assessing the efficacy of the therapeutic treatment. Such assessment of efficacy may be based on any number of assessment results. Depending on the level of efficacy assessed, the dosage of the neuroprotective peptides of this disclosure may be adjusted up or down, as needed.

Thus, by "in combination with," it is not intended to imply that the peptides of this disclosure and additional agent or therapy must be administered at the same time or formulated for delivery together, although these methods of delivery are within the scope of this disclosure. Furthermore, it will be appreciated that therapeutically active agents utilized in combination may be administered together in a single composition or administered separately in different compositions. In general, each agent will be administered at a dose and/or on a time schedule determined for that agent.

In general, each agent (in this context, one of the "agents" is a peptide of this disclosure) will be administered at a dose and on a time schedule determined for that agent. Additionally, this disclosure encompasses the delivery of the compositions in combination with agents that may improve their bioavailability, reduce or modify their metabolism, inhibit their excretion, or modify their distribution within the body.

The particular combination of therapies (e.g., therapeutics or procedures) to employ in a combination regimen will take into account compatibility of the desired therapeutics and/or procedures and the desired therapeutic effect to be achieved. In general, it is expected that agents utilized in combination will be utilized at levels that do not exceed the levels at which they are utilized individually. In some embodiments, the levels utilized in combination will be lower than those utilized individually.

Diagnosis

In one embodiment, the inventive treatment method additionally comprises diagnosing a subject with a neurological injury, disorder or neurodegenerative disease, or, during treatment, diagnosing, or evaluating or monitoring the efficacy of the treatment method. Stroke may be diagnosed by medical history and physical exam, brain computed temography, magnetic resonance imaging, computed tomography arteriogram and magnetic resonance arteriogram, carotid ultrasound, carotid angiography, EKG (Electrocardiogram), Echocardiography, and/or blood tests.

Compositions for Treating and Administration

Compositions for treating neurological injuries, diseases, and disorders, and enhancing cognitive functions of this disclosure may be formulated according to any of the conventional methods known in the art and widely described in the literature. Thus, the active ingredient (e.g., a peptide of this disclosure) may be incorporated, optionally together with other active substances, with one or more conventional pharmaceutically acceptable carriers, diluents and/or excipients, etc., appropriate for the particular use of the composition, to produce conventional preparations that are suitable or may be made suitable for administration. Carriers may include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®. They may be formulated as liquids, as semi-solids or solids, liquid solutions, dispersions, suspensions, and the like, depending on the intended mode of administration and therapeutic application. In some embodiments, the inventive composition is prepared in a form of an injectable or infusible solution. Peptides of this disclosure may be formulated in a "liposome" which is a small vesicle composed of various types of lipids, phospholipids and/or surfactant which is useful for delivery of a drug (such as an inhibitory peptide of this disclosure) to a mammal. The components of the liposome are commonly arranged in a bilayer formation, similar to the lipid arrangement of biological membranes.

Compositions of this disclosure may include a carrier protein, such as serum albumin (e.g., HSA, BSA, and the like). The serum albumin may be purified or recombinantly produced. By mixing the neuroprotective polypeptide(s) in the pharmaceutical composition with serum album, the neuroprotective polypeptides may be effectively "loaded" onto the serum albumin, allowing a greater amount of neuroprotective polypeptide to be successfully delivered to a site of neurological injury.

Methods of treating neurological injuries, diseases, or neurodegenerative diseases of this disclosure may include administration of a peptide of this disclosure via any one of a variety of routes, including intravenous (IV), intramuscular (IM), intra-arterial, intramedullary, intrathecal, subcutaneous (SQ), intraventricular, transdermal, interdermal, intradermal, by intratracheal instillation, bronchial instillation, and/or inhalation; as a nasal spray, and/or aerosol, and/or through a portal vein catheter. Any appropriate site of administration may be used. For example, the composition may be administered locally and directly at the site where action is required or may be attached or otherwise associated, e.g. conjugated, with entities which will facilitate the targeting to an appropriate location in the body.

In these compositions, any physiologically compatible carrier, excipient, diluent, buffer or stabilizer may be used. Examples of suitable carriers, excipients, diluents, buffers and stabilizers include one or more of water, saline, phosphate buffered saline, dextrose, glycerol, ethanol and the like, as well as combinations thereof. In some cases, isotonic agents, e.g., sugars, polyalcohols (e.g., mannitol, sorbitol), or sodium chloride may be included. In certain embodiments, the compositions of this disclosure may be formulated so as to provide quick, sustained, or delayed release of the active ingredient (peptides of this disclosure, or variants thereof and/or additional drug(s)) after administration to the subject by employing procedures well known in the art. As described above, in certain embodiments, the composition is in a form suitable for injection and suitable carriers may be present at any appropriate concentration, but exemplary concentrations are from 1% to 20%, or from 5% to 10%.

Therapeutic compositions typically must be sterile and stable under conditions of manufacture and storage. Appropriate ways of achieving such sterility and stability are well known and described in the art.

Pharmaceutical compositions are typically formulated in unit dosage form for ease of administration and uniformity of dosage. It will be understood, however, that the total daily (or other) usage of the compositions of the present disclosure will be decided by the attending physician within the scope of sound medical judgment. The specific therapeutically-effective dosage level for any particular subject will depend upon a variety of factors including the activity of the composition employed; the half-life of the composition after administration; the age, body weight, general health, sex, and diet of the subject; the time of administration, route of administration, and rate of excretion of the peptide and (if used) the additional therapeutic agent employed; the duration of the treatment; drugs used in combination or coincidental with the specific compound employed; and like factors, well known in the medical arts. Furthermore, effective doses may be extrapolated from dose-response curves derived from in vitro and/or in vivo animal models.

Thus, suitable doses of the peptide of this disclosure and other active ingredients (if included) will vary from patient to patient and will also depend on the severity/stage of the stroke. In some embodiments, said dosages constitute a therapeutically effective amount or a prophylactically effective amount, depending on the nature of the treatment involved. In related embodiments, the dosages constitute a neuro-restorative- or rehabilitation-enhancing amount. The ability of the peptide to elicit a desired response in the individual will also be a factor. Exemplary daily doses are: 0.1 to 250 mg/kg, or 0.1 to 200 or 100 mg/kg, or 0.5 to 100 mg/kg, or 1 to 50 or 1 to 10 mg/kg, of the active ingredient. This may be administered as a single unit dose or as multiple unit doses administered more than once a day, for example, subcutaneously, intraperitoneally, or intravenously. It is to be noted, however, that appropriate dosages may vary depending on the patient, and that for any particular subject, specific dosage regimes should be adjusted over time according to the individual needs of the patient. For example, the dosage and administration protocol may be adjusted over time, or with patient advances in rehabilitation to less than once daily, including for example, every other day, three times weekly, or two times weekly, or once weekly, or every other week, etc. Thus, the dosage ranges set forth herein are to be regarded as exemplary and are not intended to limit the scope or practice of the claimed compositions or methods.

Kits for Treating Neurological Injuries, Neurological Disease, or Neurodegenerative Diseases In one aspect, this disclosure further provides kits for the treatment of neurological injury, neurological diseases, or neurodegenerative diseases comprising a peptide of this disclosure, or variants thereof, or a composition comprising the same. Kits may include one or more other elements including, but not limited to, instructions for use; other therapeutic agents (i.e., for combination or emergency therapy of stroke); other reagents, e.g., a diluent, devices or other materials for preparing composition for administration; pharmaceutically acceptable carriers; and devices or other materials for administration to a subject. Instructions for use may include instructions for therapeutic application, including suggested dosages and/or modes of administration, e.g., in a human subject, as described herein. In some embodiments, the kits are for use in the methods and uses as described herein, e.g. therapeutic, diagnostic, or imaging methods, or are for use in in vitro assays or methods.

In some embodiments, the kits are for diagnosing neurological diseases, disorders or impairments and optionally comprise instructions for use of the kit components to diagnose or evaluate the severity of such neurological diseases, disorders or impairments.

Animal Models

As noted above, one major hurdle in improving prognosis for subjects with a neurological injury, including stroke, is the lack of a therapeutic time window. By the time of diagnosis, permanent neurological damage may have been sustained by the stroke victim. A discrepancy between experimental success in vitro and in vivo and disappointment in clinical trials likely results from the inefficiency of current experimental setups in recreating the microenvironment around the stroke.

Models of stroke in animals are critical to the pre-clinical testing of potential therapeutic compounds. The transient focal ischemia model is considered the gold standard for drug development in stroke and neuroprotection. TRPM2 inhibitory peptides of this disclosure reduced injury after reperfusion in the transient focal ischemia model.

Thus, another aspect of this disclosure provides a screening tool to identify small-molecules that specifically inhibit the TRPM2 channel by disrupting the ligand (ADPribose)-binding pocket of the TRPM2 channel, preventing activation. This screening tool comprises screening for molecules that disrupt binding of the cloned TRPM2 channel with a TRPM2 peptide inhibitor (such as the tatM2NX) of this disclosure.

EXAMPLES

The following examples are provided for illustrative purposes only and are not intended to limit the scope of this disclosure. All data are presented as mean±SEM. Each n represents an individual culture for in vitro experiments and an individual animal for in vivo experiments. All experiments were performed in a randomized and blinded manner, with analysis and surgery performed by separate investigators. Statistical significance was determined using students t-test (unpaired, 2-tailed) for 2 groups and one-way analysis of variance (ANOVA) with Newman-Keuls post hoc analysis for studies with greater than 2 groups. Statistical significance was established at $p<0.05$.

Example 1: Tat-M2NX Inhibits the Human TRPM2 Channel In Vitro

We reasoned that a mimetic peptide that disrupts the ADPr binding pocket would be a potent and specific inhibitor of TRPM2 channels. We generated a cell permeable peptide-inhibitor of TRPM2 by fusing a portion of the C-terminus, 1386-GSREPGEMLPRKLKRVLRQEFWV-OH (SEQ ID NO:1) that corresponds to the Nudix domain (nudix domain=M2NX) of the NUDT9-H region of the C-terminus of TRPM2 channels with the TAT inducer of HIV, YGRKKRRQRRR (SEQ ID NO:2). We predicted that the M2NX peptide would act as a mimetic peptide, interacting with several residues within NUDT9-H to disrupt the ADPribose binding pocket. In addition, a control peptide, which contained the same amino acids in a scrambled sequence ("tat-SCR"), was generated. In order to determine the ability of this peptide construct, having the sequence of SEQ ID NO: 3 ("tat-M2NX") to inhibit TRPM2 channels consistently among species, we used the human embryonic kidney-293 (HEK-293) cell line stably expressing tetracycline-induced human FLAG-tagged TRPM2 channel (hTRPM2).

HEK-293 cells stably expressing tetracycline-regulated cytomegalovirus-driven transcription of FLAG-tagged human TRPM2 were used. TRPM2 expressing HEK-293 cells were grown in Dubelcco's modified Eagle's medium supplemented with 10% fetal bovine serum, L-glutamine (2 mM), and penicillin/streptomycin (100 units/mL) at 37° C. in a 5% CO2 incubator. Growth medium was supplemented with Blasticidin S (InvivoGen, 5 µg/mL) and Zeocin (InvivoGen, 0.4 mg/mL) to promote stable TRPM2 expression.

HEK cells were seeded in 96-well plates coated with poly-D-Lysine (0.1 mg/mL) at 25,000 cells/well in media containing doxycycline (1 µg/mL) to drive TRPM2 expression 24 hrs prior to experiments. Cells were pre-incubated for 2 or 5 hrs with 50 µL of doxycycline-containing media with tat-M2NX (25, 50, and 100 µM), tat-SCR (25, 50, and 100 µM) or vehicle. Fluo-5F, AM (Life Technologies, 10 µM), a membrane permeable $Ca^{2+}$ indicator, was added to the media during the last 30 min of incubation. Cells were washed twice and placed in 50 µL of saline solution (135 mM NaCl, 5 mM KCl, 1 mM $MgCl_2$, 1 mM $CaCl_2$, 10 mM HEPES; pH 7.4). Baseline fluorescence was established using a microplate reader (BioTek Synergy 2) and Gen5 software to measure fluorescence (485/20, 528/20). Cells were exposed to excitation wavelengths every 20 sec for 2 min followed by $H_2O_2$ application (200 µM final concentration) or saline (control) to wells and recorded every 20 sec for 10 min.

Figure 1B:
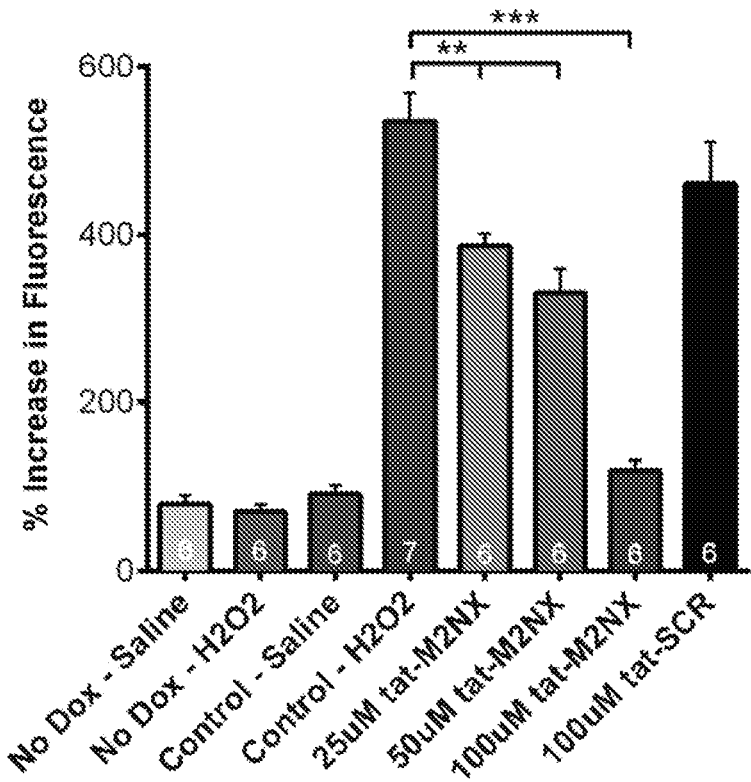
FIG. 1B shows quantification of percentage increase in Fluo-5F fluorescence in HEK-293 cells treated with 25, 50, 100 μM tat-M2NX or 100 μM tat-SCR.
Figure 1C:
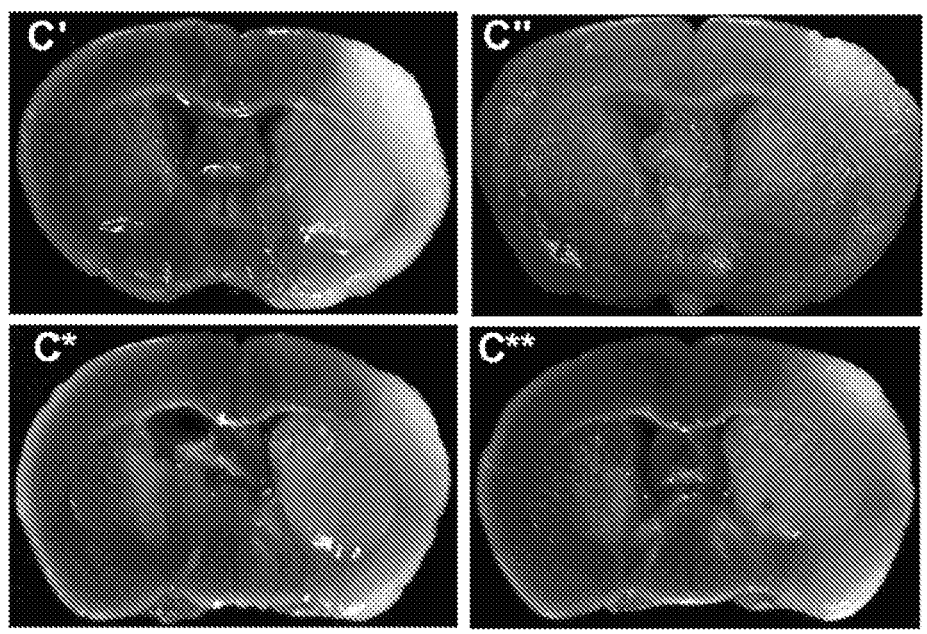
FIG. 1C provides photographs that show TTC staining from male brains treated with (C') tat-SCR and (C") tat-M2NX, and female brains treated with (C*) tat-SCR and (C**) tat-M2NX 60 minutes prior to MCAO.

TRPM2 channel activity was measured using the $Ca^{2+}$ indicator Fluo-5F to monitor changes in fluorescence detected as an increase in intracellular $Ca^{2+}$ following treatment with 200 µM $H_2O_2$. Exposure to $H_2O_2$ increased fluorescence in HEK-293 cells expressing hTRPM2, while no changes were observed in non-induced HEK-293 cells, indicating functionality of the channel in the in vitro system (FIGS. 1A & B). HEK-293 expressing the hTRPM2 had reduced H2O2-induced $Ca^{2+}$ influx after 2 hrs incubation with 100 µM tat-M2NX, while treatment with the tat-SCR peptide had no effects in $H_2O_2$-induced $Ca^{2+}$ influx via TRPM2 channel activation. Further experiments revealed a concentration-dependent decrease in $Ca^{2+}$ influx following exposure to 25, 50, and 100 µM tat-M2NX in hTRPM2 expressing HEK-293 cells (FIGS. 1A and 1B). These data demonstrate that tat-M2NX inhibits human TRPM2 channels and provides an additional tool to evaluate the role of TRPM2 channels following ischemia.

Example 2: Tat-M2NX Reduces Infarct Volume in Male Brains, but not Female Brains The inventors previously demonstrated TRPM2-related neuroprotection in vitro and reduction in infarct volume in vivo using the anti-fungal, clotrimazole (CTZ). To investigate the effects of tat-M2NX on ischemic injury following stroke, we subjected WT male and female mice to 60 min transient middle cerebral artery occlusion (tMCAO) and analyzed total hemisphere infarct volume. tat-M2NX or tat-SCR was injected 20 min prior to occlusion of the MCA and infarct volume was analyzed 24 h after reperfusion.

Transient focal cerebral ischemia (60 min) was induced using reversible MCAO through the intra-luminal filament techniques described previously (Shimizu T, Macey T A, Quillinan N, Klawitter J, Perraud A-L L, Traystman R J, et al. *Androgen and parp-1 regulation of trpm2 channels after ischemic injury*. Journal of Cerebral Blood Flow & Metabolism. 2013; 33:1549-1555). Briefly, mice were anesthetized with isoflurane delivered through a face mask (5% induction and 1-2% maintenance). Head temperature was monitored using a probe placed adjacent to the left tympanic membrane and body temperature was monitored using a rectal probe. Temperatures were maintained at 36.5±1.0° C. throughout the MCAO surgery with electrical heating pads and heating lamp. A laser-Doppler probe (model, Moor Instruments, Oxford, England, UK) was affixed to the right skull to monitor cortical perfusion and to verify vascular occlusion and reperfusion. A skin incision was made in the middle of the anterior neck. After the right common carotid artery was tightened using 6-0 silk suture, a 6-0 nylon monofilament with a silicone-coated tip was inserted into the right internal carotid artery via the external carotid artery until the laser-Doppler flowmetry (LDF) value decreased to less than 20% of baseline. After securing the filament in place, the incision was closed with 6-0 silk suture. Each mouse was placed in a separate cage, with a warm water pad under the cage. At the end of the period of occlusion, the mice were re-anesthetized while the laser-Doppler probe was re-positioned over the same site on the right skull, and the occluding filament was withdrawn for reperfusion. The mice were then allowed to recover under observation.

After the corresponding reperfusion period, the mice were anesthetized with 5% isoflurane and decapitated for brain collection. The mice were excluded from the study if subarachnoid hemorrhage was observed. Each cerebrum was sliced into four 2-mm-thick coronal sections. The sections were placed in 1.2% of 2,3,4-triphenyltetrazolium chloride for 30 min at 37° C. and fixed in 10% formalin for 24 h. Each coronal slice was stained and photographed on both sides using a digital camera, infarction was measured with ImageJ (NIH, Bethesda, Md., USA), and integrated across all five slices. In order to include the effect of edema, the infarct volume was estimated indirectly and plotted as percentage of the contralateral structure and is presented as a corrected hemisphere infarct.

tat-M2NX or tat-SCR peptides were dissolved in saline (5 mg/mL), and injected retro-orbitally (20 mg/kg) at timing indicated. Briefly, animals were anesthetized with 4% isoflurane in the induction box for 3 min, and placed in left lateral position with the head facing to the right. An insulin syringe (BD Ultra-fine Needle 12.7 mm×30 G) was inserted at a 45° angle into the retro-bulbar space. The tip of the needle was introduced to penetrate the retro-orbital sinus and inject solution. After injection, the needle was carefully removed keeping the bevel outward to protect the eyes from being scratched.

Figure 1D:
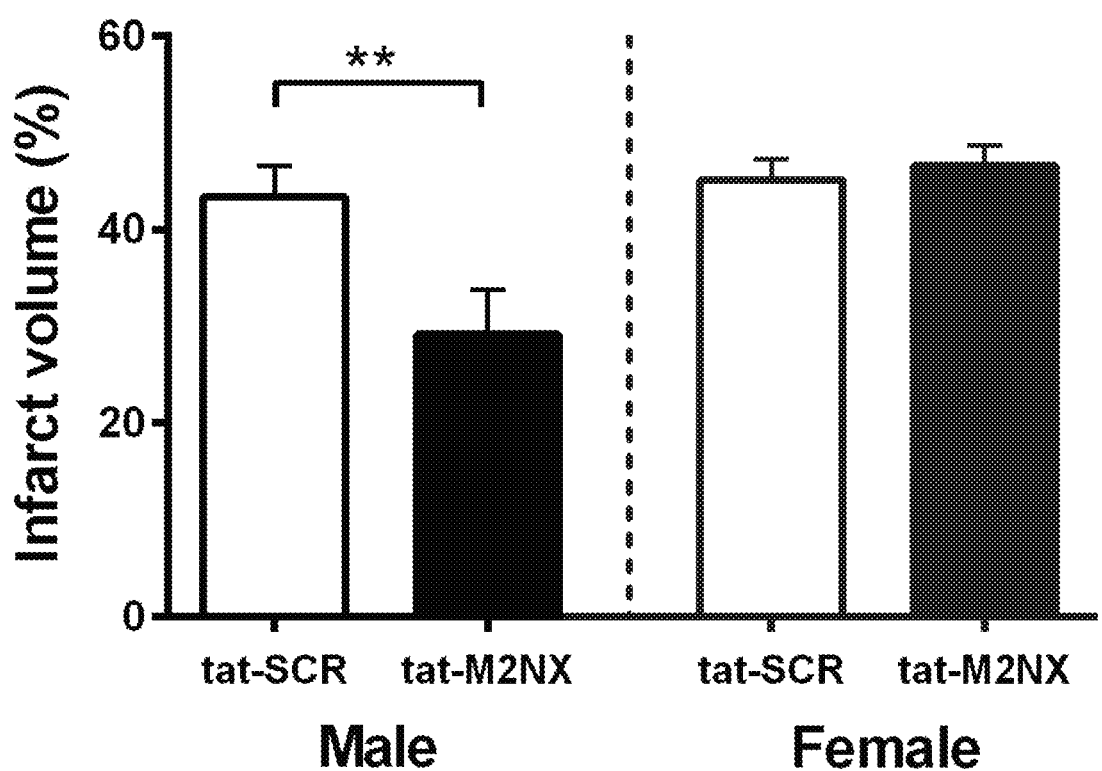
FIG. 1D shows quantification of percentage of infarct volume in WT male and female mice treated with vehicle, 100 μM tat-SCR, or 100 μM tat-M2NX.

MCA occlusion was similar between male and female mice measured by doppler flow and there was no effect of tat-M2NX on physiological variables such as blood pressure. Males that were treated with tat-M2NX showed smaller infarct volume compared to tat-SCR (29.2±4.6% [n=8] vs. 43.4±3.2% [n=8; p<0.01]), respectively (FIG. 1D). In contrast, there was no difference in infarct size after stroke in female mice exposed to tat-SCR (46.6±2.1% [n=7]) or tat-M2NX (45.1±2.1% [n=7], FIG. 1D). Together, these data demonstrate the ability of tat-M2NX to inhibit TRPM2 channel activity in vivo and produce male-specific neuroprotection, as previously described using CTZ.

Figure 2:
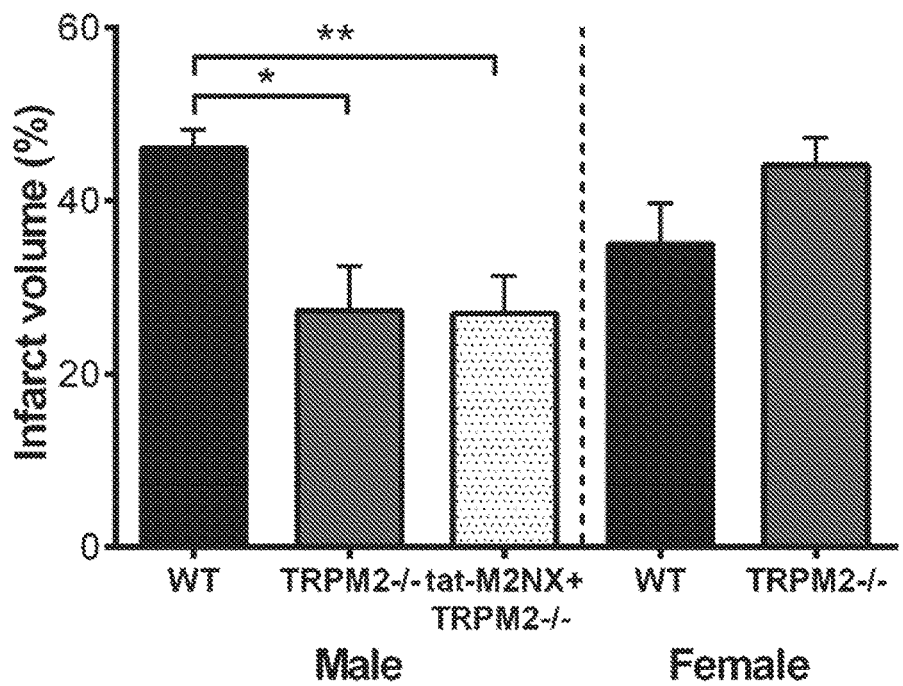
FIG. 2 shows tat-M2NX does not protect TRPM2−/− mice following 60 min tMCAO. Quantification of percentage of infarct volume from WT and TRPM2−/− mice brains stained with TTC. TRPM2−/− male mice were treated with 100 μM tat-M2NX peptide or vehicle.

Example 3: Tat-M2NX Provides No Further Protection Compared to TRPM2 Knockout To further characterize the specificity of tat-M2NX for TRPM2 channels, we compared the neuroprotective efficacy of tat-M2NX to that of TRPM2 knock out mice (TRPM2−/−). Infarct volume was reduced in male TRPM2−/− compared to WT male mice, 27.3±5.1% (n=8) vs. 46.1±6.0% (n=7; p<0.05), respectively (FIG. 2). There was no difference in infarct volume observed between WT and TRPM2−/− females, (35.0±4.6% [n=9] vs. 44.2±3.2% [n=6], FIG. 2). Administration of tat-M2NX did not further reduce infarct volume in male TRPM2−/−, providing further evidence of specificity for TRPM2 channels by tat-M2NX.

Example 4: Tat-M2NX Demonstrates a Translation-Relevant Therapeutic Window

Figure 3A:
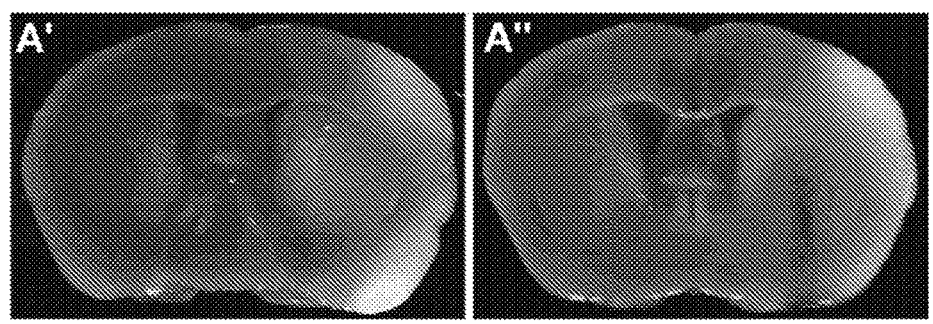
FIG. 3A shows tat-M2NX exhibits a clinically relevant therapeutic window, as representative TTC staining of male mice treated with tat-SCR (A') or tat-M2NX (A") 3 hours after reperfusion and stained 24 hours after reperfusion.
Figure 3B:
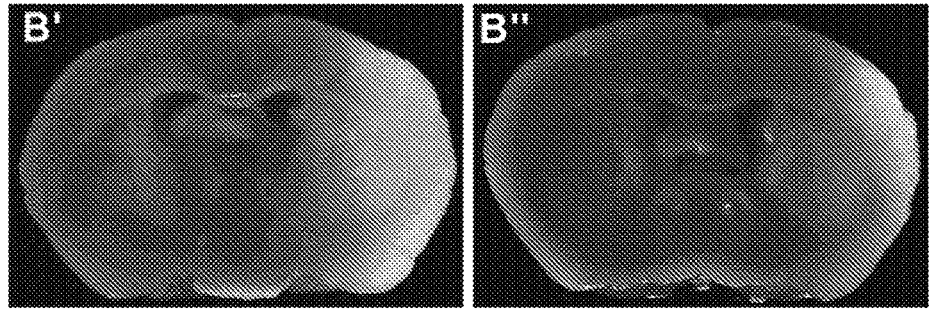
FIG. 3B shows male mice treated with tat-SCR (B') or tat-M2NX (B") 3 hours after repurfusion and stained 96 hours after reperfusion.
Figure 3C:
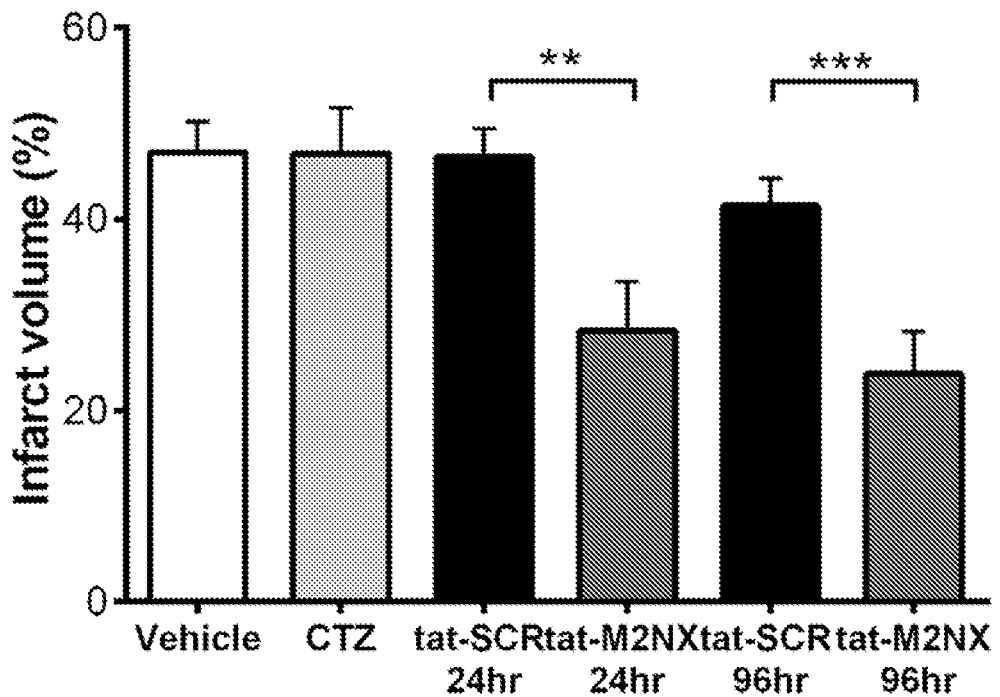
FIG. 3C shows the quantification of percentage of infarct volume in male and female brains stained with TTC 24 hrs and 96 hrs after receiving drug. Male and female mice were treated with vehicle, clotrimazole (CTZ), tat-SCR (20 mg/kg) or tat-M2NX (20 mg/kg).

Clinical trials in stroke have failed for a variety of reasons, but many have failed due to a relevant therapeutic window. The standard of care for pharmacologic intervention after ischemic stroke remains tissue plasminogen activator (tPA) given within 3-4.5 hours of symptom onset. Therefore, we tested whether tat-M2NX administered 3 hours after reperfusion (4 hours after onset of ischemia) in WT male mice can provide neuroprotection. tat-M2NX or tat-SCR was administered intravenously 3 hours post-reperfusion and the brain was collected at either 24 h or 96 h after injection to analyze the extent of infarct size. tat-M2NX significantly reduced infarct volume at 24 hr and 96 hr post-stroke compared to tat-SCR (FIG. 3C, 24 h: tat-SCR 46.5±7.3% (n=6) vs tat-M2NX 28.3±13.5% (n=7, p<0.05); 96 h: tat-SCR 41.4±8.0% (n=8) vs tat-M2NX 23.8±12.5% (n=8, p<0.05)). In contrast, administration of the non-selective TRPM2 inhibitor clotrimazole (CTZ) 3 hours after MCAO had no effects on infarct volume (FIG. 3C, Vehicle 47.0±9.9% vs CTZ 46.8±7.4%). These data show that not only is tat-M2NX neuroprotective, but also has a wider therapeutic window than CTZ and is similar to the clinical intervention of tPA.

Example 5: Tat-M2NX Provides Neuroprotection in Aged Male Mice

Figure 4:
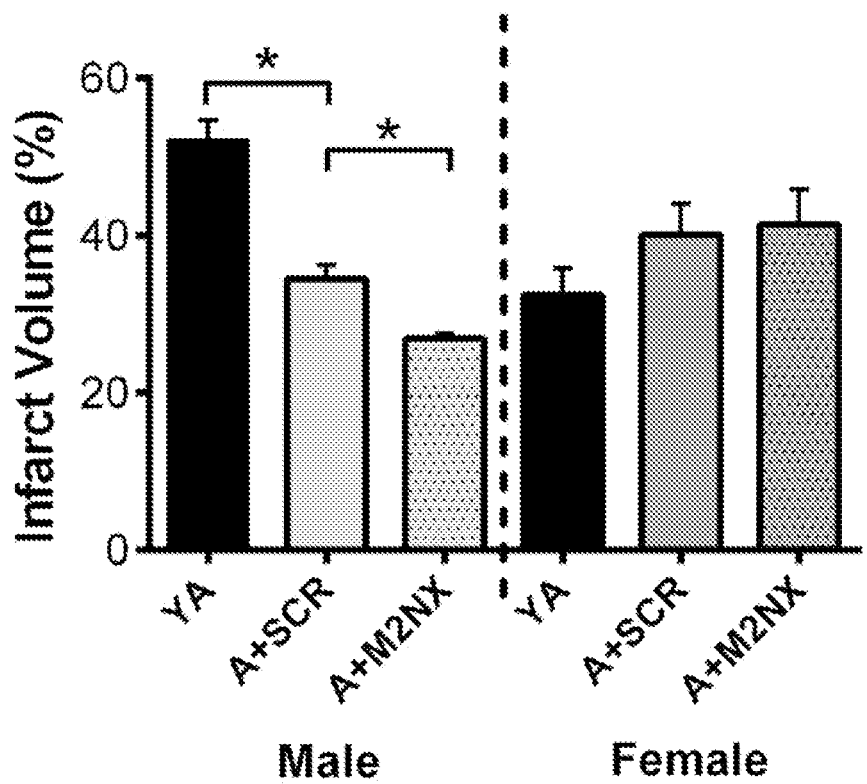
FIG. 4 shows tat-M2NX provides neuroprotection in aged males, as the quantification of percentage of infarct in 18-20 month old male and female mice receiving either tat-SCR (SCR) or tat-M2NX (M2NX). YA=young adult; A=aged. *p<0.05.

The incidence of stroke increases with age among all races and both sexes. Therefore, we tested whether tat-M2NX would provide protection in aged mice. 18-20 month-old male and female mice were subjected to 60 min MCAO and tat-M2NX or tat-SCR was administered 30 min after reperfusion. Infarct volume was analyzed 24 hours later. Consistent with the data from young adults, aged male mice given tat-M2NX had smaller infarct volumes compared to aged males given tat-SCR (27.0±0.7% [n=6] vs. 34.6±1.7% [n=6], respectively [FIG. 4]; p<0.01). Interestingly, control aged male mice (tat-SCR treated) had smaller infarcts compared to young adult (YA) mice, consistent with previous reports (REFS: McCullough) (27.0±0.7% [n=6] vs. 52.1±2.7% [n=6], respectively (FIG. 4). In contrast, tat-M2NX did not provide neuroprotection in aged females compared to tat-SCR (40.2±4.0% [n=6] vs. 41.5±4.5% [n=6], FIG. 4). Together, these data suggest that TRPM2 channels contribute to acute ischemic cell death following stroke in aged males, but not in females.

Example 6: Tat-M2NX Blocks TRPM2 Channels and Reduces Infarct Volume in Males, but not Females Our studies made use of aged animals to demonstrate continued efficacy in older animals. Though there is a need for aged animal studies in preclinical studies, relatively few studies report the interaction between age and treatment. This issue is particularly relevant given the changes in androgen levels at older ages and the activation of TRPM2 channels by androgen related pathways. It has previously been demonstrated that protection following TRPM2 inhibition in males requires the presence of androgens, as castration removes the protection and DHT replacement rescues the protection observed following CTZ administration. We speculated that low androgens in aged male mice would cause loss of tat-M2NX neuroprotection. Therefore, we assessed serum levels of testosterone and the higher potency dihydrotestosterone (DHT) across the mouse lifespan.

A cohort of naïve male mice was sacrificed by Avertin overdose (intraperitoneal) for blood sample collections from the right ventricle of the heart using heparinized syringes. The blood sample was centrifuged at 3300 g for 10 minutes at 4° C. to yield serum for hormone detection. Serum was stored at −80° C. until use. Enzyme-linked immunoassay for testosterone (Calbiotech, Spring Valley, Calif., USA) and Dihydrotestoserone (DHT, Alpha Diagnostic International, Tex.) were performed following the manufacturers' protocols.

Figure 5A:
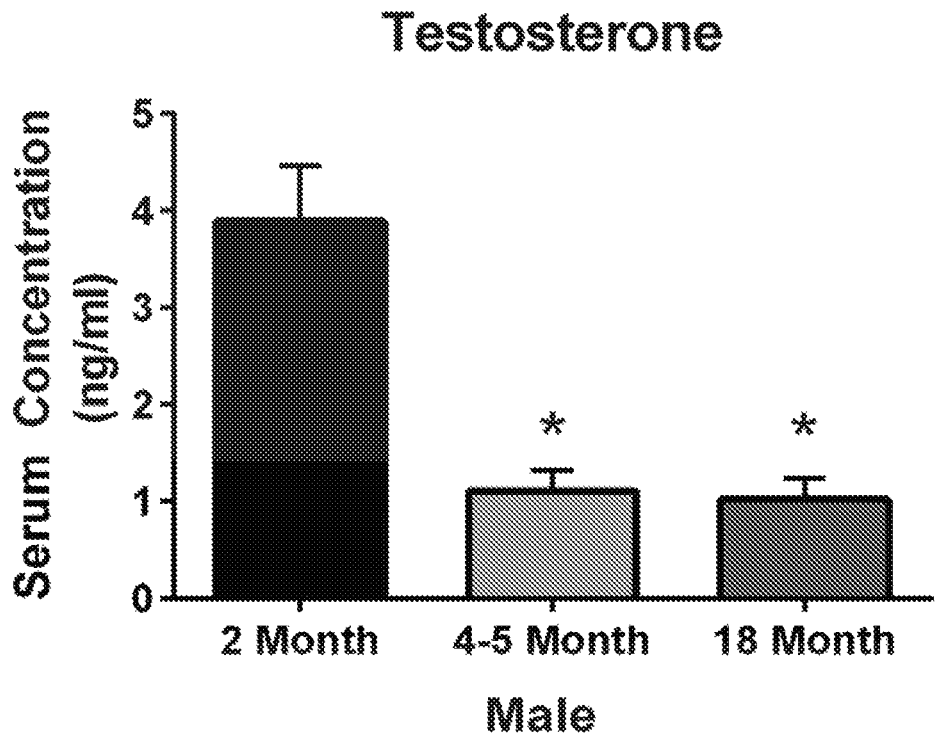
FIG. 5A shows that testosterone, but not dihydrotestosterone, decreases with age in male mice, as the quantification of serum concentration of testosterone measured by ELISA in male mice aged 2 months, 4-5 months, and 18 months.
Figure 5B:
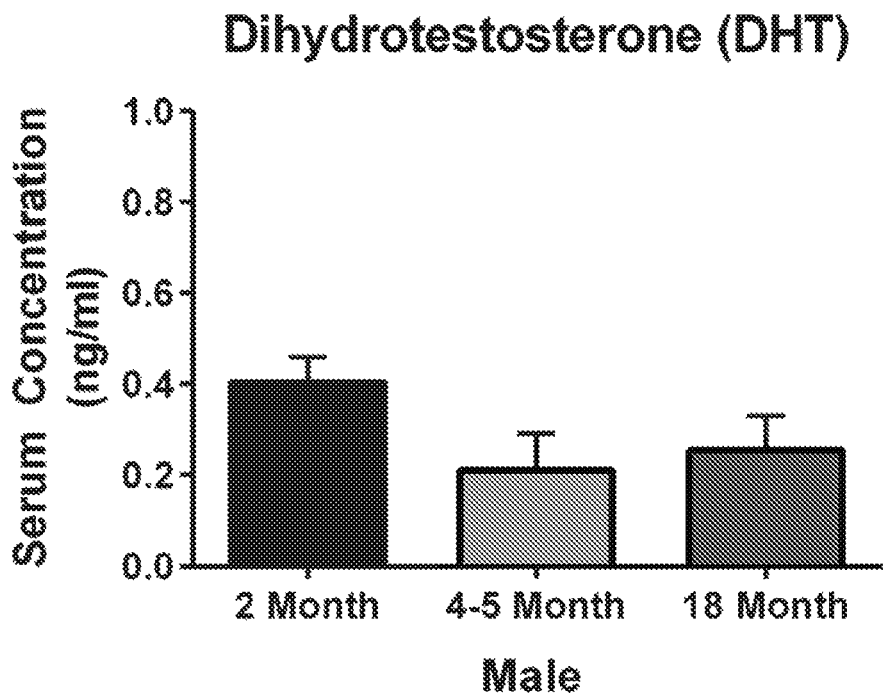
FIG. 5B shows the quantification of serum concentration of dihydrotestosterone (DHT) measured by ELISA in male mice aged 2 months, 4-5 months, and 18 months. *p<0.05.
Figure 6A:
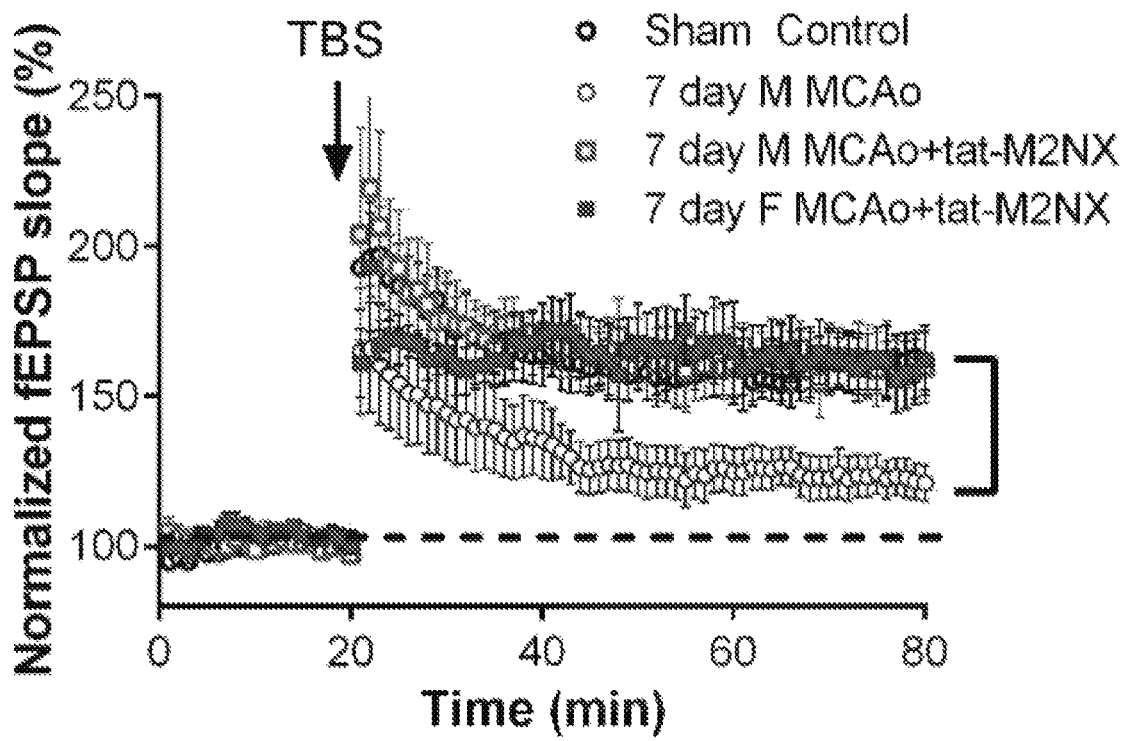
FIGS. 6A and 6B demonstrate the reversal of ischemia-induced impairment of synaptic plasticity following delayed administration of tat-M2NX.
Figure 6B:
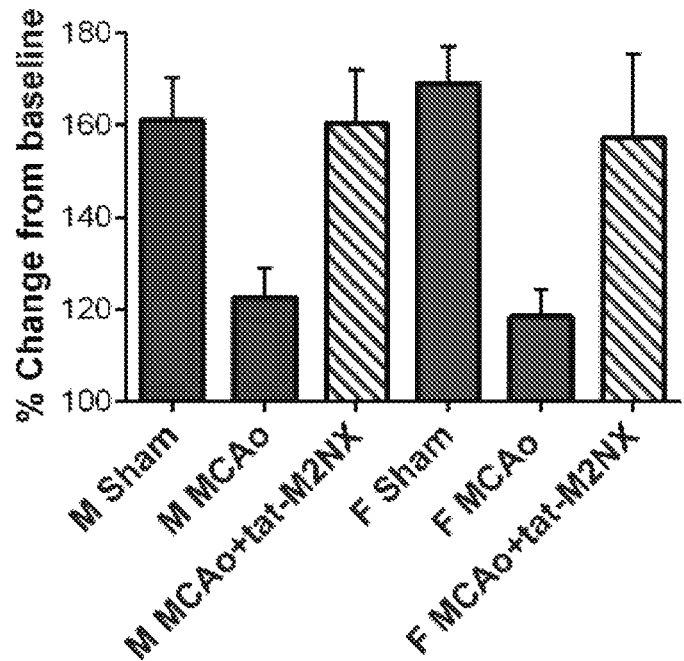

Testosterone levels were decreased in older mice (FIG. 5A) compared to young adults, however there was no change across ages in the higher potency dihydrotestosterone (DHT) (FIG. 5B), suggesting that DHT levels remain sufficiently high to engage TRPM2 channels in aged male mice. Together, the data presented here represent an important pre-clinical study using a novel peptide to block TRPM2 channels and reduce infarct volume in males, but not females.

Example 7: TRPM2 Inhibition Reduces Cardiac Arrest-Induced Neuronal Injury

The 34-mer, TRPM2 inhibitor of this disclosure: YGRKKRRQRRRGSREPGEMLPRKLKRVLRQEFWV (SEQ ID NO:3; "tat-M2NX") was tested for the ability to reduce cardiac arrest/cardiopulmonary resuscitation (CA/CPR)-induced neuronal injury in male and female mice. To determine protective efficacy, we administered either 20 mg/kg scrambled control (tat-SCR) or 20 mg/kg tat-M2NX via intravenous (iv) injection 30 minutes after resuscitation from 8 min cardiac arrest in male and female mice. Quantification of ischemic CA1 neurons using hematoxylin and eosin (H&E) staining 3 days after resuscitation showed that iv injection of tat-M2NX provides robust protection against ischemic injury in male mice (reducing injury from 44.9±7.5% (n=12) in tat-SCR treated males to 20.0±5.1% (n=12, P<0.05) in tat-M2NX treated males), while having no effect on injury in the female (FIGS. 6A, 6B, 7A, 7B). In addition, as we previously reported in experimental stroke, we observed significantly reduced CA1 neuronal injury in TRPM2 KO male mice compared with male WT controls, while CA1 injury in female TRPM2 KO and WT mice were not different. Data generated using lower doses of tat-M2NX demonstrated neuroprotection following MCAo in male mice at doses as low is 1 mg/kg.

Figure 7A:
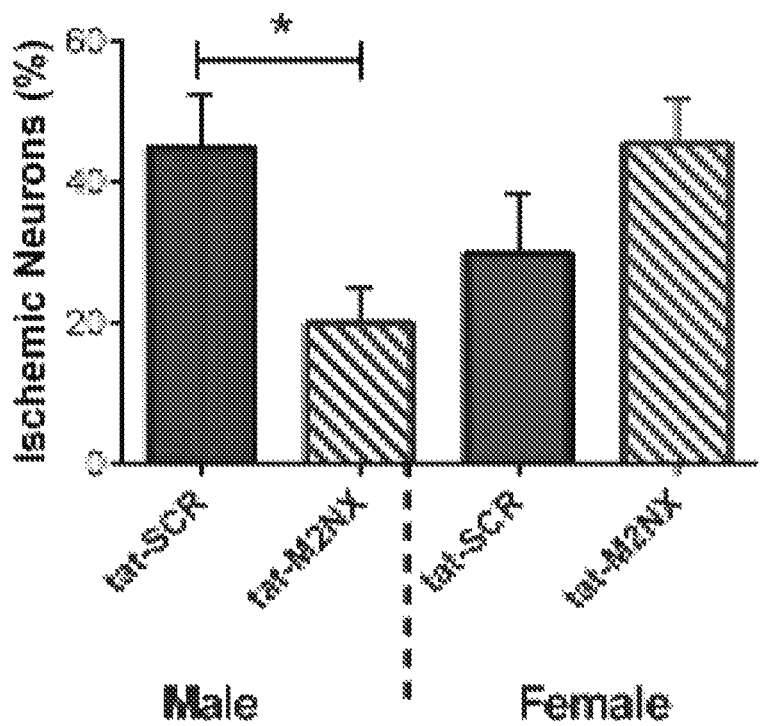
FIGS. 7A and 7B demonstrate tat-M2NX reduction of CA1 neuronal injury and improvement in long-term synaptic function, in male mice specifically.
Figure 7B:
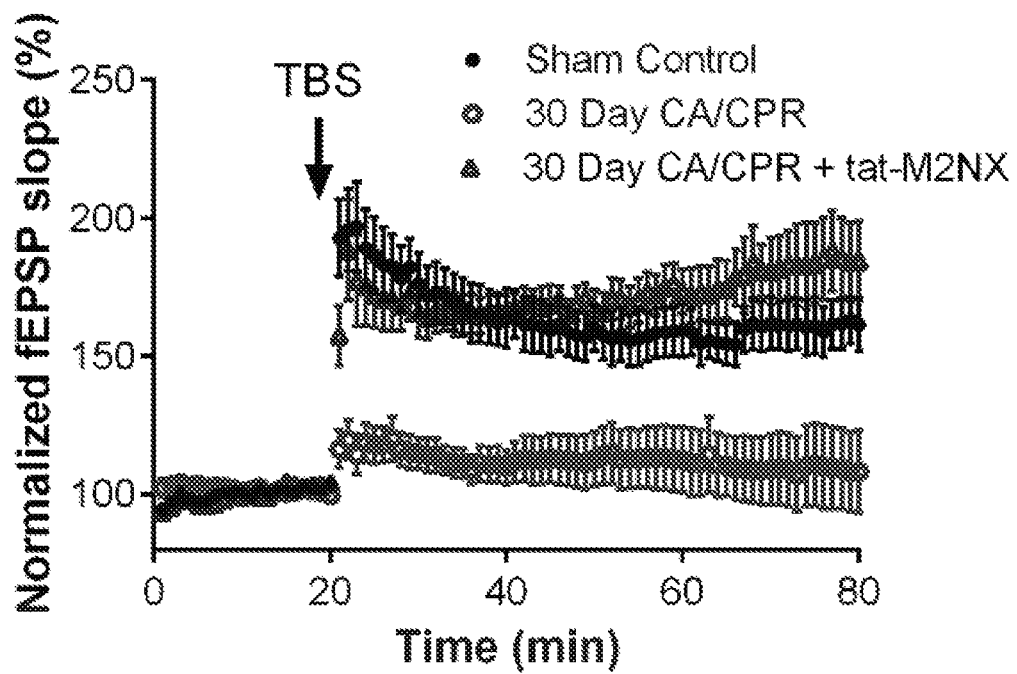
Figure 8A:
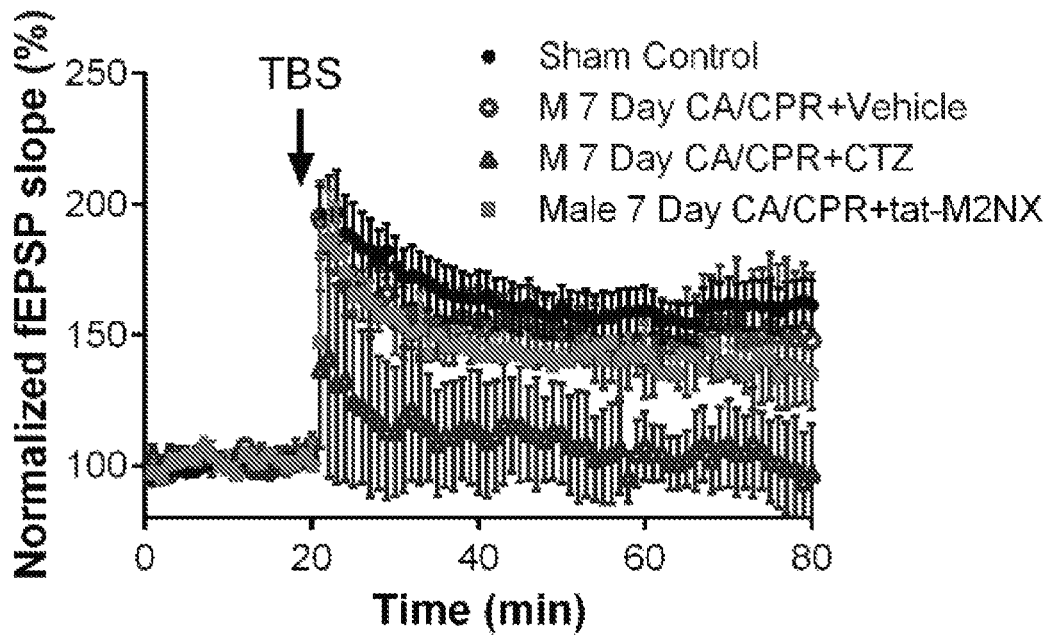
FIGS. 8A and 8B demonstrate inhibition of TRPM2 in acute slices reverses ischemia-induced impairment of synaptic plasticity.
Figure 8B:
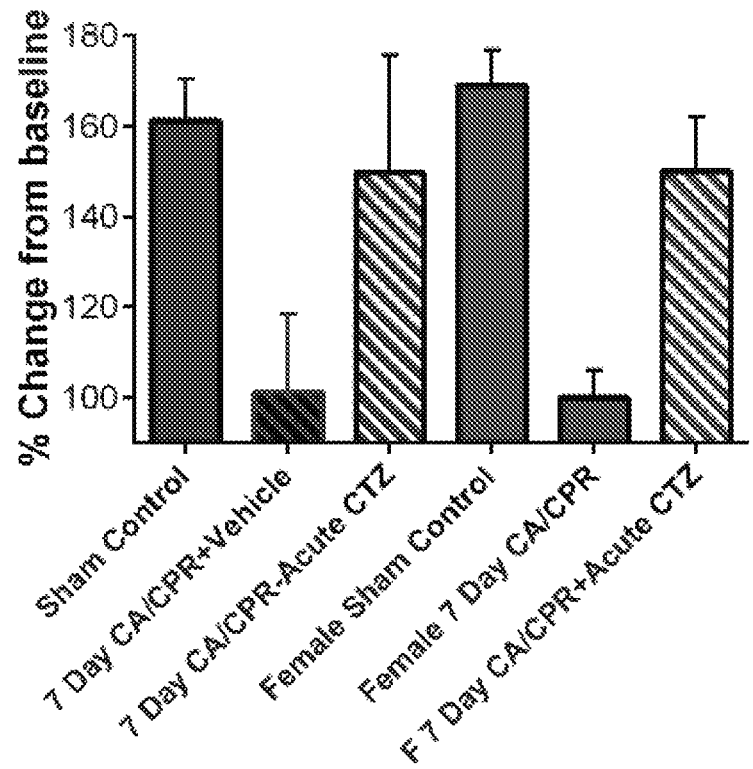

Following our report that ischemia induced by CA/CPR causes impaired hippocampal synaptic plasticity for at least 30 days, we also observed no changes in NMDA receptor function (or pre-synaptic release, excitability), implicating other signaling pathways in the LTP impairment. Therefore, to begin to determine whether acute administration of tat-M2NX provides sustained functional benefit in male animals, we performed extracellular field recordings of CA1 neurons to measure synaptic plasticity after CA/CPR in tat-SCR and tat-M2NX treated mice. Schaffer collateral (CA3 axons) to CA1 field excitatory post-synaptic potentials (fEPSPs) were recorded. In sham control slices, after a 20 min stable baseline, a brief physiological theta burst simulation (TBS: 40 pulses at 10 Hz) increased the slope of fEPSP to 161±9.2% (n=6, P<0.05 compared to baseline) that was sustained for the entire 60 minutes of recording, thus termed LTP (FIG. 7A—black trace). In contrast, recordings obtained from brain slices from post-ischemic mice treated with control peptide (tat-SCR) exhibited a near complete loss of LTP when cells were exposed to the identical TBS stimulus, (7 day: 105.0±8.6% (n=8); 30 day: 109.2±14.2% (n=7; FIG. 2), both P<0.05 compared to sham control). Importantly, control electrophysiology experiments demonstrate minimal effects of CA/CPR on pre-synaptic release (PPR), AMPA/NMDA ratio or overall excitability (I/O) 10. Recordings from hippocampal slices taken from mice 7 or 30 days after CA/CPR and treated with tat-M2NX (30 min post-CA) exhibited LTP following TBS indistinguishable from sham controls (7 day: 188.1±22.0% (n=5); 30 day: 184.0±13.8% (n=5; FIGS. 8A and 8B), both not significant compared to sham control and P<0.05 from each group's baseline). These experiments demonstrate that post-ischemic administration of tat-M2NX provides sustained protection of synaptic function and improves cognitive outcomes.

Figure 9A:
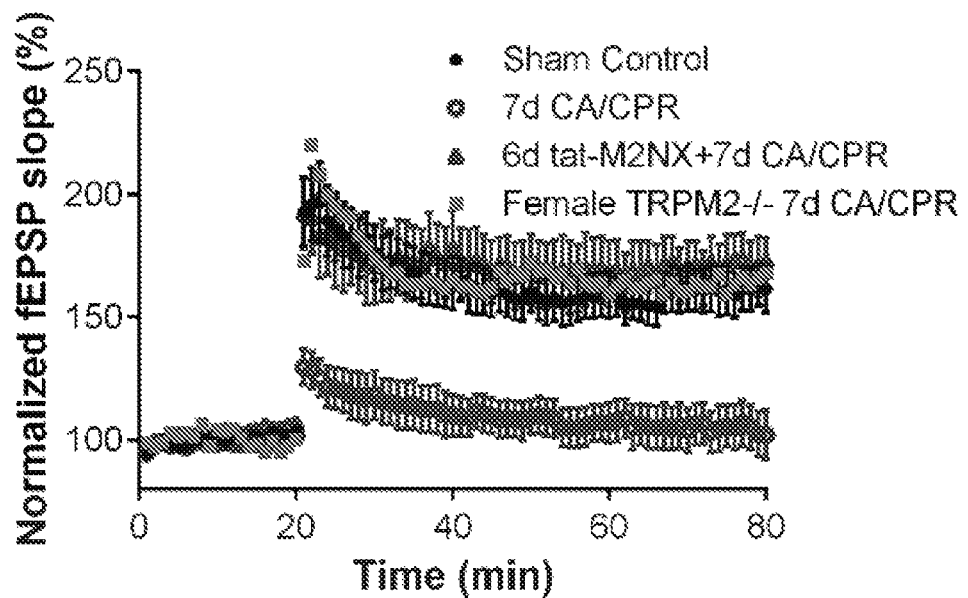
FIGS. 9A and 9B demonstrate delayed administration of tat-M2NX reverses ischemia-induced impairment of synaptic plasticity.
Figure 9B:
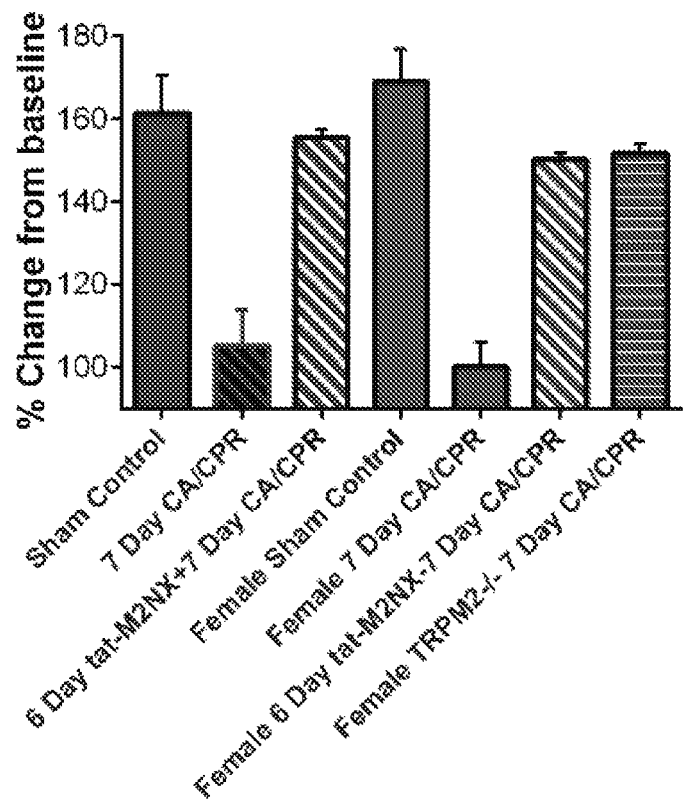

Example 8: Inhibition of Persistent Activation of TRPM2 Channels Following Ischemia Improves Memory Function and Synaptic Plasticity To assess whether TRPM2 channels play a role in ischemia-induced impairment in synaptic plasticity, we inhibited TRPM2 channels in brain slices obtained days after suffering an ischemic brain injury. Consistent with the data described above, recordings obtained in brain slices from mice 7 days after CA/CPR exhibited a near complete loss of LTP when cells were exposed to the same TBS stimulation that stimulates robust LTP in sham control mice (FIGS. 9A and 9B). Remarkably, bath application of the TRPM2 channel inhibitor clotrimazole (CTZ; 20 µM) for 1 hour reversed the CA/CPR-induced loss of LTP, recovering to 149.8±26% (n=3; P<0.05 compared to paired 7 day CA/CPR slices recorded from the same animal on the same day). Further, we made the very surprising observation that CTZ rescued CA/CPR-induced loss of LTP in females equally as effectively, recovering to 150.1±17% (n=2; FIG. 8B). Post-ischemic slices were incubated for 2 hours in 1 µM tat-M2NX and synaptic plasticity was measured. FIG. 8A (red trace) demonstrates reversal of deficit following exposure of tat-M2NX (n=3). This provocative data has two major implications: 1) CA/CPR causes persistent activation of TRPM2 channels in hippocampal CA1 neurons in both male and females and 2) TRPM2 channel activity in the hippocampus during the sub-acute to chronic phase of recovery after cerebral ischemia inhibits synaptic plasticity.

To confirm the role of sustained TRPM2 channel activity in impaired synaptic plasticity we performed additional experiments to assess the ability of delayed administration of tat-M2NX to rescue hippocampal function in vivo. Mice were subjected to 8 min cardiac arrest and CPR and administered tat-M2NX (20 mg/kg) 6 days after resuscitation. 24 hours after tat-M2NX administration (7 days post-CA/CPR), acute hippocampal slices were obtained and field recordings were made to assess synaptic plasticity (LTP). FIGS. 9A and 9B illustrate our exciting finding that delayed administration of tat-M2NX in vivo reverses CA/CPR-induced impairments in hippocampal LTP, recovering to 171±11% (n=6 recordings from 4 mice treated with peptide; P<0.05 compared to 7 day CA/CPR slices). FIG. 9B further demonstrates that we extended this observation by confirming that delayed tat-M2NX treatment in vivo rescues synaptic plasticity in male and female mice, recovering female LTP to 170±16% (n=3). The ability of tat-M2NX to reverse CA/CPR-induced impairments in LTP in vivo indicates this is a viable approach to improve functional recovery at delayed time-points. FIGS. 9A (red trace) and 9B shows CA/CPR does not impair LTP in female TRPM2−/− mice, consistent with a role of TRPM2 in impaired LTP independent of neuronal injury, as female TRPM2−/− mice exhibit the same extent of injury as WT female mice.

Figure 10A:
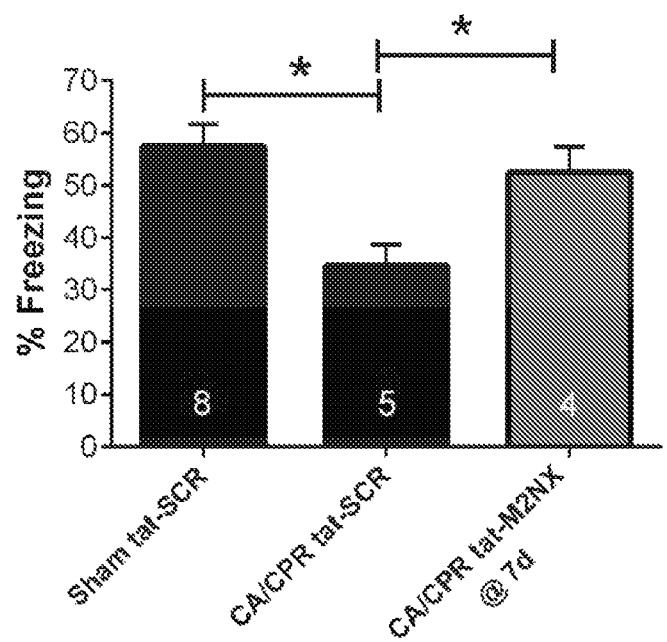
FIGS. 10A and 10B demonstrate delayed administration of tat-M2NX reverses ischemia-induced memory impairment.
Figure 10B:
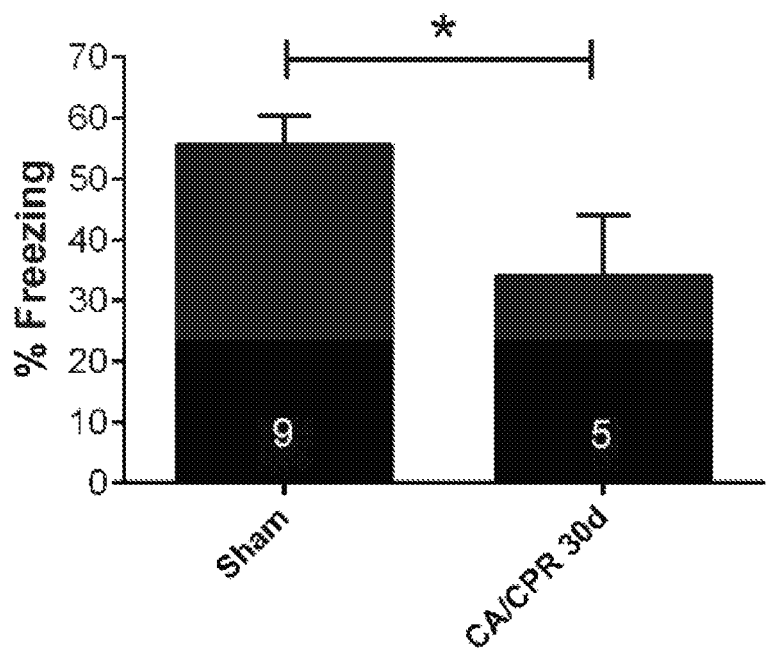

Importantly, delayed administration of tat-M2NX improves memory function in post-ischemic mice. We took advantage of the well-established hippocampal memory task, contextual fear conditioning (CFC). Briefly, mice were exposed to a novel environment and, after habituation in the environment, given a mild foot shock (1 mA) and then returned to their home cage. 24 hr after the foot shock, mice are placed again in the CFC environment and freezing behavior is analyzed during a 10 min test. Memory of the environment evokes a freezing behavior, as seen in sham mice (FIG. 10A). In contrast, CA/CPR causes a significant reduction in freezing behavior (FIG. 10A), indicating a loss of memory. Importantly, hippocampal-dependent memory deficit is observed at both 7 (FIG. 10A) and 30 days (FIG. 10B) after CA/CPR. Preliminary experiments indicate that delayed administration of tat-M2NX (on day 7), improves memory function (FIG. 10A), consistent with our synaptic plasticity experiments described above (FIGS. 9A and 9B).

Example 9: Inhibition of TRPM2 Enhances Neurological Function Following Traumatic Brain Injury (TBI)

Figure 11A:
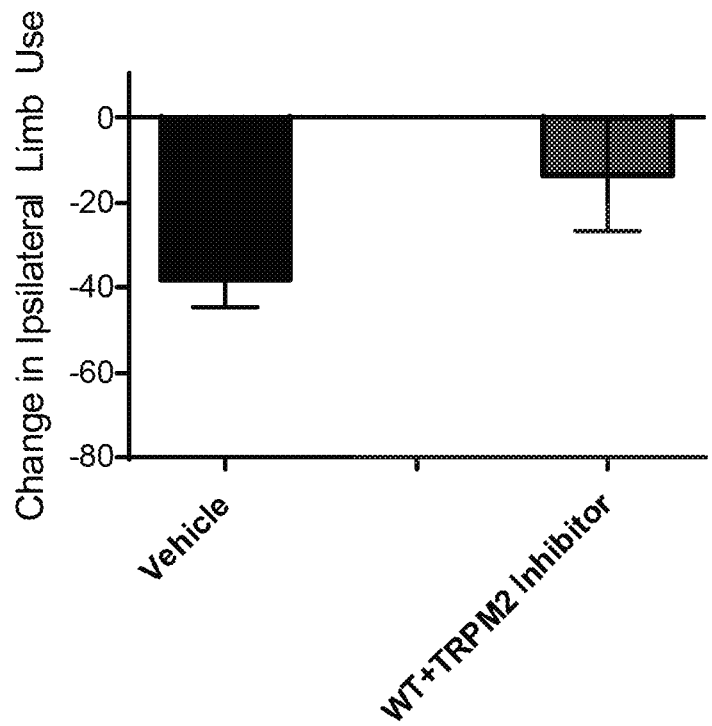
FIGS. 11A and 11B show the effects of TRPM2 channel inhibition by tat-M2NX on motor and memory function in mice following traumatic brain injury.
Figure 11B:
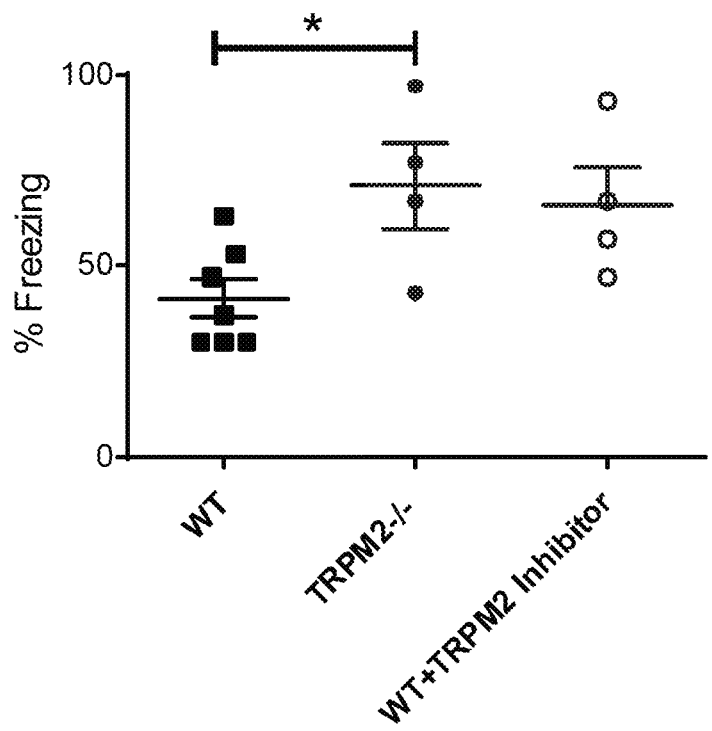

A mouse model of moderate/severe traumatic brain injury was used. The Controlled Cortical Impact (CCI) model was used, and our tat-M2NX TRPM2 inhibitor was injected immediately after the TBI was administered in this model. Motor function and memory function analyses were performed 7 days after recovery from TBI. The motor function is analyzed using the cylinder test, which measures limb use and a decrease in contralateral limb use (in this case left paw use because of R cortical injury), indicating motor deficit. The memory function test is the contextual fear conditioning (CFC) task, described above. FIG. 11A shows improved motor function and FIG. 11B shows improved memory function in mice treated with the TRPM2 inhibitor (also TRPM2 KO mice in the case of memory) following TBI. Additionally, as demonstrated in FIG. 9, TRPM2 inhibition reversed TBI-induced LTP deficits.

Figure 12A:
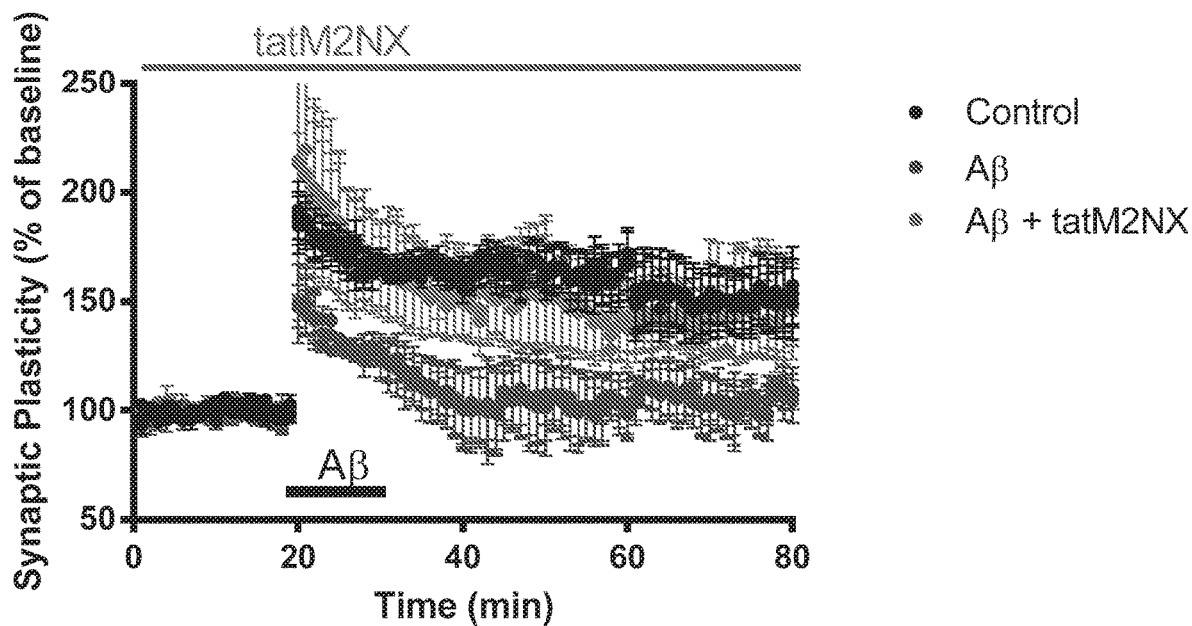
FIGS. 12A and 12B demonstrate inhibition of TRPM2 in acute slices reverses ischemia-induced impairment of synaptic plasticity.
Figure 12B:
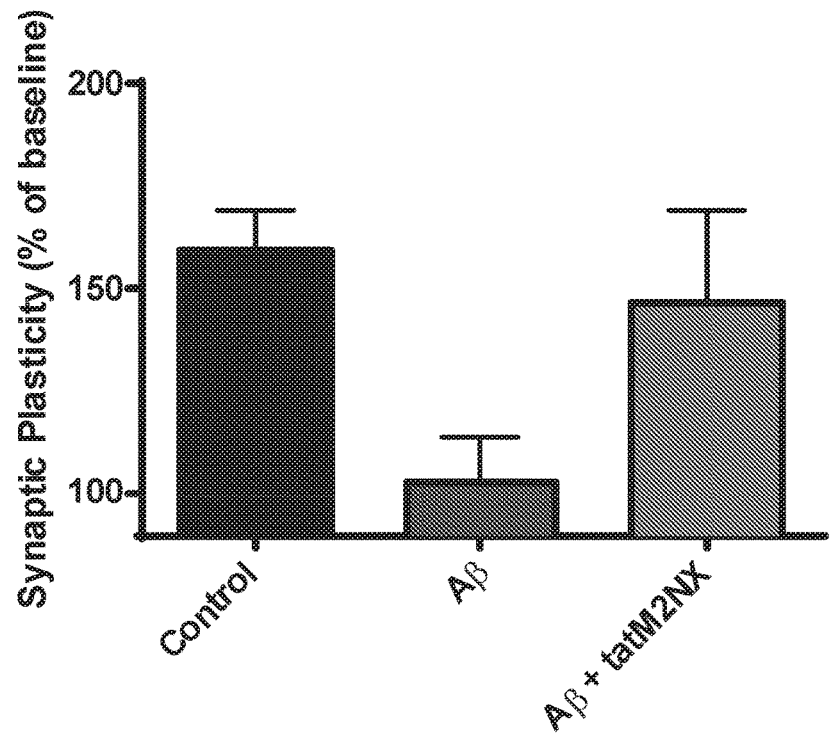

Example 10: Inhibition of TRPM2 Channels Prevents Beta-amyloid-induced Decrease in Synaptic Plasticity To assess whether TRPM2 channels play a role in amyloid-induced impairment in synaptic plasticity, we inhibited TRPM2 channels in brain slices that were exposed to amyloid beta. Recordings obtained in brain slices from mice in the absence or presence of beta-amyloid and a TRPM2 peptide inhibitor of this disclosure (tatM2NX) (FIG. 12A) showed that TRPM2 channel inhibition protected against beta-amyloid-induced decrease in synaptic plasticity (FIG. 12B), showing that the peptides of this disclosure are useful in treating or slowing the progress of Alzheimer's disease.

The present disclosure is not to be limited in scope by the specific embodiments described herein which are intended as single illustrations of individual aspects of this disclosure, and functionally equivalent methods and components are within the scope of this disclosure. Indeed, various modifications of this disclosure, in addition to those shown and described herein will become apparent to those skilled in the art from the foregoing description and accompanying drawings. Such modifications are intended to fall within the scope of the claims.

The invention claimed is:

1. An isolated peptide, wherein the isolated peptide is the amino acid sequence GSREPGEMLPRKLKRVLRQEFWV (SEQ ID NO:1), or KLKRVLRQEFWV (SEQ ID NO. 12).

2. The peptide of claim 1, wherein the peptide is SEQ ID NO: 1 linked to an internalization peptide selected from the group consisting of HIV TAT sequence (YGRKKRRQRRR; SEQ ID NO:2), or variants thereof, XGRKKRRQRRR (SEQ ID NO:4; in which X is an amino acid other than Y), FGRKKRRQRRR (SEQ ID NO:5), GRKKRRQRRR (SEQ ID NO:6), and GSRVQIRCRFRNSTR (SEQ ID NO:11).

3. The peptide of claim 2, wherein the peptide is linked to the internalization peptide through a linker selected from Gly(Ser)$_4$ (SEQ ID NO:7), TGEKP (SEQ ID NO:8), GGRRGGGS (SEQ ID NO:9), and LRQRDGERP (SEQ ID NO:10).

4. The peptide of claim 1, wherein the peptide comprises the ability to inhibit the flux of calcium ions through a TRPM2 protein ion channel.

5. A composition comprising a peptide of claim 1, and at least one pharmaceutically acceptable excipient.

* * * * *

SEQUENCE LISTING

```
<160> NUMBER OF SEQ ID NOS: 11

<210> SEQ ID NO 1
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 1

Gly Ser Arg Glu Pro Gly Glu Met Leu Pro Arg Lys Leu Lys Arg Val
1               5                   10                  15

Leu Arg Gln Glu Phe Trp Val
            20

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Tyr Gly Arg Lys Lys Arg Arg Gln Arg Arg Arg
1               5                   10

<210> SEQ ID NO 3
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 3

Tyr Gly Arg Lys Lys Arg Arg Gln Arg Arg Gly Ser Arg Glu Pro
1               5                   10                  15

Gly Glu Met Leu Pro Arg Lys Leu Lys Arg Val Leu Arg Gln Glu Phe
            20                  25                  30

Trp Val

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa Gly Arg Lys Lys Arg Arg Gln Arg Arg Arg
1               5                   10
```

```
<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 5

Phe Gly Arg Lys Lys Arg Arg Gln Arg Arg Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Gly Arg Lys Lys Arg Arg Gln Arg Arg Arg
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 7

Gly Ser Ser Ser Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Thr Gly Glu Lys Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Gly Gly Arg Arg Gly Gly Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 10

Leu Arg Gln Arg Asp Gly Glu Arg Pro
1               5
```

```
<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

Gly Ser Arg Val Gln Ile Arg Cys Arg Phe Arg Asn Ser Thr Arg
1               5                   10                  15
```